(12) United States Patent
Ben-Maimon et al.

(10) Patent No.: US 7,772,219 B2
(45) Date of Patent: Aug. 10, 2010

(54) METHODS OF HORMONAL TREATMENT UTILIZING EXTENDED CYCLE CONTRACEPTIVE REGIMENS

(75) Inventors: Carole S. Ben-Maimon, Merion, PA (US); Howard Hait, Wilmington, DE (US); Kathleen Z. Reape, Bryn Mawr, PA (US); Lance J. Bronnenkant, Synder, NY (US)

(73) Assignee: Teva Women's Health, Inc., Woodcliff Lake, NJ (US)

( * ) Notice: Subject to any disclaimer, the term of this patent is extended or adjusted under 35 U.S.C. 154(b) by 1636 days.

(21) Appl. No.: 10/837,268

(22) Filed: May 3, 2004

(65) Prior Publication Data

US 2004/0220152 A1 Nov. 4, 2004

Related U.S. Application Data

(60) Provisional application No. 60/524,081, filed on Nov. 24, 2003, provisional application No. 60/467,172, filed on May 2, 2003.

(51) Int. Cl.
*A61K 31/56* (2006.01)
*A61K 31/58* (2006.01)

(52) U.S. Cl. .................. 514/170; 514/171; 514/841; 514/874; 514/843; 514/178

(58) Field of Classification Search .................. 514/170, 514/171, 178, 841, 843, 874
See application file for complete search history.

(56) References Cited

U.S. PATENT DOCUMENTS

| | | | |
|---|---|---|---|
| 3,568,828 A * | 3/1971 | Lerner .................... 206/528 |
| 4,145,416 A | 3/1979 | Lachnit-Fixson et al. |
| 4,171,358 A * | 10/1979 | Black ..................... 514/178 |
| 4,758,592 A * | 7/1988 | Horrobin et al. ............. 514/549 |
| 4,962,098 A | 10/1990 | Boissonneault |
| 5,043,331 A | 8/1991 | Hirvonen et al. |
| 5,208,225 A | 5/1993 | Boissonneault et al. |
| 5,296,230 A * | 3/1994 | Chien et al. ................. 424/448 |
| 5,552,394 A | 9/1996 | Hodgen |
| 5,567,695 A | 10/1996 | Labrie |
| 5,753,639 A | 5/1998 | Labrie |
| 5,898,032 A | 4/1999 | Hodgen |
| RE36,247 E | 7/1999 | Plunkett et al. |

(Continued)

FOREIGN PATENT DOCUMENTS

EP 0 253 607 A1 1/1988

(Continued)

OTHER PUBLICATIONS

Kousta et al. (Human Reproduction Update, 1997, 3, pp. 359-365).*

(Continued)

*Primary Examiner*—Sreeni Padmanabhan
*Assistant Examiner*—Umamaheshwari Ramachandran
(74) *Attorney, Agent, or Firm*—Sterne, Kessler, Goldstein & Fox P.L.L.C.

(57) ABSTRACT

The present invention provides extended cycle contraceptive regimens in which a female is administered a combined dosage form of estrogen and progestin. The disclosed extended cycle contraceptive regimens can be administered to a female as a method of providing non-contraceptive benefits.

7 Claims, 2 Drawing Sheets

U.S. PATENT DOCUMENTS

| | | | |
|---|---|---|---|
| 6,028,064 | A | 2/2000 | Rodriguez et al. |
| 6,139,873 | A * | 10/2000 | Hughes et al. ............... 424/464 |
| 6,251,956 | B1 | 6/2001 | Kafrissen et al. |
| 6,265,393 | B1 | 7/2001 | Heinrichs |
| 6,306,914 | B1 | 10/2001 | de Ziegler et al. |
| 6,319,911 | B1 | 11/2001 | Rodriguez |
| RE37,838 | E | 9/2002 | Spona et al. |
| 6,451,779 | B1 | 9/2002 | Hesch |
| 6,500,814 | B1 | 12/2002 | Hesch |
| 6,511,970 | B1 | 1/2003 | Rodriguez |
| 6,569,857 | B1 * | 5/2003 | Hermelin et al. ............ 514/249 |
| 6,667,050 | B1 | 12/2003 | Boissonneault et al. |
| 6,787,531 | B1 | 9/2004 | Hilman et al. |
| RE39,861 | E | 9/2007 | Hodgen |
| 7,297,688 | B2 | 11/2007 | Grubb |
| 7,320,969 | B2 | 1/2008 | Bell et al. |
| 2001/0020015 | A1 | 9/2001 | Kafrissen et al. |
| 2002/0132801 | A1 | 9/2002 | Heil et al. |
| 2002/0169205 | A1 * | 11/2002 | Chwalisz et al. ............ 514/509 |
| 2003/0018018 | A1 | 1/2003 | Hodgen et al. |
| 2003/0114429 | A1 | 6/2003 | Hilman et al. |
| 2003/0119798 | A1 | 6/2003 | Heil et al. |
| 2003/0139381 | A1 | 7/2003 | Bell et al. |
| 2003/0144258 | A1 | 7/2003 | Heil et al. |
| 2003/0216366 | A1 | 11/2003 | Leonard et al. |
| 2003/0229057 | A1 | 12/2003 | Caubel et al. |
| 2004/0009960 | A1 | 1/2004 | Heil et al. |
| 2004/0142914 | A1 | 7/2004 | Friedman et al. |
| 2004/0222123 | A1 | 11/2004 | Niemann |
| 2004/0251301 | A1 | 12/2004 | Niemann et al. |
| 2005/0051454 | A1 | 3/2005 | Coe et al. |

FOREIGN PATENT DOCUMENTS

| | | |
|---|---|---|
| EP | 0 911 029 B1 | 9/2003 |
| WO | WO 93/17686 A1 | 9/1993 |
| WO | WO 98/04246 A2 | 2/1998 |
| WO | WO 00/38691 A1 | 7/2000 |
| WO | WO 2004/080442 A1 | 9/2004 |
| WO | WO 2005/032558 A1 | 4/2005 |

OTHER PUBLICATIONS

Gitsch et al. (Fertility and Sterility, 29, 2, 1978).*

Branigan et al. (Fertility and Sterility, 71, 3, Mar. 1999).*

"Headaches: OCs are 'guilty by association'," *Contraceptive Technology Update* 14(7):109-112, Thomson American Health Consultants (1993).

Goldzieher, J.W., "Use and Misuse of the Term Potency with Respect to Oral Contraceptives," *J. Reproductive Med.* 31:533-539, The Journal of Reproductive Medicine, Inc. (1986).

King, R.J.B., and Whitehead, M.I., "Assessment of the potency of orally administered progestins in women," *Fertility and Sterility* 46:1062-1066, Elsevier for the American Society for Reproductive Medicine (1986).

Komaat, H., et al., "The Acceptance of a 7-Week Cycle with a Modern Low-Dose Oral Contraceptive (Minulet®)," *Contraception* 45:119-127, Elsevier (1992).

Mashchak, C.A., et al., "Comparison of pharmacodynamic properties of various estrogen formulations," *Am. J. Obstet. Gynecol.* 144:511-518, The C.V. Mosby Co. (1982).

Miller, L., and Notter, K.M., "Menstrual Reduction With Extended Use of Combination Oral Contraceptive Pills: Randomized Controlled Trial," *Obstet. Gynecol.* 98:771-778, Lippincott, Williams & Wilkins (Nov. 2001).

Phillips, A., et al., "A Comparison of the Potencies and Activities of Progestogens Used in Contraceptives," *Contraception* 36:181-192, Geron-X, Inc. (1987).

Piper, J.M., and Kennedy, D.L., "Oral Contraceptives in the United States: Trends in Content and Potency," *Intl. J. Epidemiology* 16:215-221, Oxford University Press (1987).

Shearman, R.P., "Oral contraceptive agents," *Med. J. Australia* 144:201-205, Australasian Medical Publishing (1986).

International Search Report for International Application No. PCT/US2005/035997, European Patent Office, Rijswijk, NL, mailed Apr. 7, 2006.

International Search Report for International Application No. PCT/US04/13589, ISA/US, Alexandria, VA, mailed Mar. 9, 2006.

Written Opinion of the International Searching Authority for International Application No. PCT/US04/13589, ISA/US, Alexandria, VA, mailed Mar. 9, 2006.

European Opposition Document D32, Facts About Seasonale®, 1 page, Barr Laboratories, Inc. (available after Sep. 5, 2003), cited in the Opposition to Patent No. 0 911 029 B1.

European Opposition Document D33, Seasonale® Product Brochure, 15 pages, Duramed Pharmaceuticals, Inc. (Jan. 2004), cited in the Opposition to Patent No. 0 911 029 B1.

Adams Hillard, P.J., "Oral contraception noncompliance: The extent of the problem," *Adv. Contracep.* 8(Suppl. 1):13-20, Kluwer Academic Publishers (1992).

Branigan, E.F. and Estes, M.A., "A randomized clinical trial of treatment of clomiphene citrate-resistant anovulation with the use of oral contraceptive pill suppression and repeat clomiphene citrate treatment," *Am. J. Obstet. Gynecol.* 188:1424-1430, Mosby, Inc. (Jun. 2003).

Case, A.M. and Reid, R.L., "Effects of the Menstrual Cycle on Medical Disorders," *Arch. Intern. Med.* 158:1405-1412, American Medical Association (1998).

Coffee, A., "Hormone-Based Contraception: The Extended Cycle Regimen," Supplement to *Drug Topics*, pp. 3-15, Advanstar Communications, Inc. (Jan. 2004).

Dickey, R.P., "Oral Contraception: Realizing the Promise by Overcoming the Pitfalls," *Individualizing Oral Contraceptive Therapy, OBG Management Supplement*, pp. 2-6, Watson Pharma, Inc. (Oct. 2000).

European Opposition Document, Notice of Opposition (Article 99 and Rule 55 EPC), submitted by Akzo Nobel N.V. in the Opposition to European Patent No. 0 911 029 B1, 8 pages (Jan. 2002).

European Opposition Document, Notice and Statement of Opposition, submitted by Schering AG in the Opposition to European Patent No. 0 911 029 B1, 32 pages (Jan. 2003).

European Opposition Document, Response to Communication of Notices of Opposition, submitted by Patentee in the Opposition to European Patent No. 0 911 029 B1, 10 pages (Oct. 2003).

European Opposition Document, Summons to Attend Oral Proceedings Pursuant to Rule 71(1) EPC, issued by European Patent Office, Netherlands, in the Opposition to European Patent No. 0 911 029 B1, 1 page (Jan. 2004).

European Opposition Document, Written Submission, with new Main and Auxiliary Requests, submitted by Patentee in the Opposition to European Patent No. 0 911 029 B1, 23 pages (Apr. 2004).

European Opposition Document, Further Written Submissions, submitted by Schering AG in the Opposition to European Patent No. 0 911 029 B1, 17 pages (Apr. 2004).

European Opposition Document, Further Submission, "Urgent—Oral Proceedings Scheduled for Jun. 8, 2004," submitted by Patentee in the Opposition to European Patent No. 0 911 029 B1, 2 pages (May 2004).

European Opposition Document, Further Submission, "URGENT: Oral Proceedings on Jun. 8, 2004," submitted by Akzo Nobel N.V. in the Opposition to European Patent No. 0 911 029 B1, 1 page (May 2004).

European Opposition Document, Further Submission, "Urgent—Oral Proceedings Jun. 8, 2004," submitted by Schering AG in the Opposition to European Patent No. 0 911 029 B1, 2 pages (May 2004).

European Opposition Document, Decision revoking the European Patent No. EP B 0 911 029 (Article 102(1),(3) EPC), issued by European Patent Office in the Opposition to European Patent No. 0 911 029 B1, Netherlands, 41 pages (Jul. 1, 2004).

European Opposition Document D1, Cachrimanidou, A.-C., et al., "Long-interval treatment regimen with a desogestrel-containing oral contraceptive," *Contraception* 48:205-216, Butterworth-Heinemann (1993), cited in the Opposition to European Patent No. 0 911 029 B1.

European Opposition Document D2, Kovacs, G.T., et al., "A trimonthly regimen for oral contraceptives," *Brit. J. Fam. Planning* 19:274-275, Faculty of Family Planning and Reproductive Health Care (1994), cited in the Opposition to European Patent No. 0 911 029 B1.

European Opposition Document D3, Davies, G.C., et al., "Ovarian Activity and Bleeding Patterns During Extended Continuous Use of a Combined Contraceptive Vaginal Ring," *Conception* 46:269-278, Elsevier (1992), cited in the Opposition to European Patent No. 0 911 029 B1.

European Opposition Document D4, "Vier keer per jaar ongesteld," *Intermediair*, 2 pages, Intermediair (May 2002), cited in the Opposition to European Patent No. 0 911 029 B1.

Partial English translation of European Opposition Document D4, "Having a period four times per year," *Intermediair*, 2 pages, Intermediair (May 2002), cited in the Opposition to European Patent No. 0 911 029 B1.

European Opposition Document D5, Loudon, N.B., et al., "Acceptability of an oral contraceptive that reduces the frequency of menstruation: the tri-cycle pill regimen," *Brit. Med. J.* 2:487-490, British Medical Association (1977), cited in the Opposition to European Patent No. 0 911 029 B1.

European Opposition Document D6, Vollebregt, J.A., et al., "A Study on Postponement of Menses with Low-Dose Combined Oral Contraceptives—Outcome and Acceptability," *Adv. Contraception* 1:207, Abstract No. 19, Kluwer Academics (1985), cited in the Opposition to European Patent No. 0 911 029 B1.

European Opposition Document D7, Omtzigt, A.M. and Boerrigter, P.J., "The effect of 30 µg ethinylestradiol/75 µg gestodene and 20 µg ethinylestradiol/150 µg desogestrel on cycle control during normal and extended oral contraceptive intake," *Eur. J. Contracept. Reprod. Health Care* 1:155, Abstract No. FC70, Parthenon Publishing (1996), cited in the Opposition to European Patent No. 0 911 029 B1.

European Opposition Document D8, Szarewski, A. and Guillebaud, J., eds., *Contraception, A User's Handbook*, Oxford University Press, Oxford, UK, pp. 46, 53, 54, 84, 87 (1994), cited in the Opposition to European Patent No. 0 911 029 B1.

European Opposition Document D9, Schneider, H.P.G., et al., eds., "Empfängnis-verhätung," Urban & Schwarzenberg, Munich, Germany, pp. 7-8 (1996), cited in the Opposition to European Patent No. 0 911 029 B1.

European Opposition Document D10, Guillebaud, J., ed., "*Contraception. Your questions answered*," Churchill Livingstone, New York, NY, pp. 75, 131, 154-155, (1986), cited in the Opposition to European Patent No. 0 911 029 B1.

European Opposition Document D11, Mishell, D.R., Jr., "Oral Contraception: Past, Present, and Future Perspectives," *Int. J. Fertil.* 36: 7-18, MSP International (1991), cited in the Opposition to European Patent No. 0 911 029 B1.

European Opposition Document D12, de Voogd, W.S., "Postponement of Withdrawal Bleeding with a Monophasic Oral Contraceptive Containing Desogestrel and Ethinylestradiol," *Contraception* 44:107-112, Elsevier (1991), cited in the Opposition to European Patent No. 0 911 029 B1.

European Opposition Document D13, Rutter, W., et al., "Women's attitudes to withdrawal bleeding and their knowledge and beliefs about the oral contraceptive pill," *Med. J. Australia* 149:417-419, Australasian Medical Publishing Co. (1988), cited in the Opposition to European Patent No. 0 911 029 B1.

European Opposition Document D14, Sulak, P.J., et al., "Extending the Duration of Active Oral Contraceptive Pills to Manage Hormone Withdrawal Symptoms," *Obstet. & Gynecol.* 89:179-182, Lippincott, Williams & Wilkins (1997), cited in the Opposition to European Patent No. 0 911 029 B1.

European Opposition Document D15, U.S. Patent No. 5,552,394, Hodgen, G.D., issued Sep. 3, 1996, cited in the Opposition to European Patent No. 0 911 029 B1.

European Opposition Document D16, Speroff, L., et al., eds., "Chapter 2. Oral Contraception," in: *A Clinical Guide for Contraception*, Lippincott, Williams & Wilkins, pp. 25-117 (2000), cited in the Opposition to European Patent No. 0 911 029 B1.

European Opposition Document D17, Düsterberg, B., et al., "Terminal Half-lives in Plasma and Bioavailability of Norethisterone, Levonorgestrel, Cyproterone acetate and Gestodene in Rats, Beagles and Rhesus Monkeys," *Contraception* 24:673-383, Elsevier (1981), cited in the Opposition to European Patent No. 0 911 029 B1.

European Opposition Document D18, Düsterberg, B., et al., "Half-lives in Plasma and Bioavailability of Ethinylestradiol in Laboratory Animals," *Drug Res.* 36:1187-1190, Edititio Cantor (1986), cited in the Opposition to European Patent No. 0 911 029 B1.

European Opposition Document D19, WIPO International Publication No. 93/17686, published Sep. 16, 1993, cited in the Opposition to European Patent No. 0 911 029 B1.

European Opposition Document D20, Letter filed by Schering AG in Opposition to EP 0686037 B1, the Medical College of Hampton Roads, 5 pages (Aug. 2003), cited in the Opposition to European Patent No. 0 911 029 B1.

European Opposition Document D21, Hamerlynck, J.V.Th.H., et al., "Postponement of Withdrawal Bleeding in Women Using Low-Dose Combined Oral Contraceptives," *Contraception* 35:199-205, Elsevier (1987), cited in the Opposition to European Patent No. 0 911 029 B1.

European Opposition Document D22, Anderson, F.D. and Hait, H., "A multicenter, randomized study of an extended cycle oral contraceptive," *Contraception* 68:89-96, Elsevier (Aug. 2003), cited in the Opposition to European Patent No. 0 911 029 B1.

European Opposition Document D23, Report of Bleeding observed with Seasonale products as compared to conventional OC products, addendum to Anderson, F.D. and Hait, H., "A multicenter, randomized study of an extended cycle oral contraceptive," *Contraception* 68:89-96, Elsevier (Aug. 2003), 2 pages, cited in the Opposition to European Patent No. 0 911 029 B1.

European Opposition Document D24, Glaser, J., "Seasonale, Market Research," carried out by Ziment Associates on behalf of Barr Laboratories, Inc. (Jan. 2003), 14 pages, cited in the Opposition to European Patent No. 0 911 029 B1.

European Opposition Document D25, "The 2003 Gallup Study of the Market for Oral Contraceptives," conducted by Multi-Sponsor Surveys, Inc., for Barr Laboratories, Inc., 17 pages (May 2003), cited in the Opposition to European Patent No. 0 911 029 B1.

European Opposition Document D26, Comparison of Seasonale with other birth control products, IMS Health, Market data from Jun. 2001-Jan. 2004, 4 pages, cited in the Opposition to European Patent No. 0 911 029 B1.

European Opposition Document D27, Declaration of Dr. Anne Szarewski, in the Matter of EP 0 911 029 B1, Medical College of Hampton Roads and Opposition Thereto by Schering AG, 8 pages, cited in the Opposition to European Patent No. 0 911 029 B1 (Apr. 2004).

Annex I of Declaration of Dr. Anne Szarewski (Document D27 in the Opposition to European Patent No. EP 0 911 029 B1), Szarewski, A.M., *Curriculum Vitae*, 14 pages.

Annex II of Declaration of Dr. Anne Szarewski (Document D27 in the Opposition to European Patent No. EP 0 911 029 B1), "Commercially Available Monophasic Combined Oral Contraceptive Pills," and "Ratio of equivalence given in patent EP 0 911 029 B1".

Annex III of Declaration of Dr. Anne Szarewski (Document D27 in Opposition to European Patent No. EP 0 911 029 B1), Belsey, E.M., "The Association Between Vaginal Bleeding Patterns and Reasons for Discontinuation of Contraceptive Use," *Contraception* 38:207-225, Elsevier (1988).

Annex IV of Declaration of Dr. Anne Szarewski (Document D27 in Opposition to European Patent No. EP 0 911 029 B1), Benagiano, G. and Fraser, I., "The Depo-Provera Debate, Commentary on the Article Depo-Provera, A Critical Analysis," in: *Contraception* 24:493-528, Elsevier (1981).

Annex V of Declaration of Dr. Anne Szarewski (Document D27 in Opposition to European Patent No. EP 0 911 029 B1), "Is Cerazette the minipill of choice?," *Drug Ther. Bull.* 41:1-3, Consumers' Association (Sep. 2003).

Annex VI of Declaration of Dr. Anne Szarewski (Document D27 in Opposition to European Patent No. EP 0 911 029 B1), Committee for Proprietary Medicinal Products, "Clinical Investigation of Steroid Contraceptives in Women," *Note for Guidance on Clinical Investigation of Steroid Contraceptives in Women*, 5 pages, The European Agency for the Evaluation of Medicinal Products (2000).

Annex VII of Declaration of Dr. Anne Szarewski (Document D27 in Opposition to European Patent No. EP 0 911 029 B1), Goldzieher, J.W. and Fotherby, K., eds., *Pharmacology of the Contraceptive Steroids*, Raven Press, New York, NY, pp. 82-86 (1994).

Annex VIII of Declaration of Dr. Anne Szarewski (Document D27 in Opposition to European Patent No. EP 0 911 029 B1), Guillebaud, J., ed., "The pill: how do I take it?," in: *The Pill and Other Hormones for Contraception*, Oxford University Press, Great Britain, UK, pp. 52-53, 110-113, 182-183, 190-191 (1991).

Annex IX of Declaration of Dr. Anne Szarewski (Document D27 in Opposition to European Patent No. EP 0 911 029 B1), Adams Hillard, P.J., "The patient's reaction to side effects of oral contraceptives," *Am. J. Obstet. Gynecol. 161*:1412-1415, Mosby-Year Book (1989).

Annex X of Declaration of Dr. Anne Szarewski (Document D27 in Opposition to European Patent No. EP 0 911 029 B1), International Working Group, "A consensus statement: enhancing patient compliance and oral contraceptive efficacy," *Brit. J. Fam. Planning 18*:126-129, Faculty of Family Planning and Reproductive Health Care (1993).

Annex XI of Declaration of Dr. Anne Szarewski (Document D27 in Opposition to European Patent No. EP 0 911 029 B1), Korver, T., for the Collaborative Study Group, "A double-blind study comparing the contraceptive efficacy, acceptability and safety of two progestogen-only pills containing desogestrel 75 µg/day or levonorgestrel 30 µg/day," *Eur. J. Contra. Reprod. Health Care 3*:169-178, Parthenon Publishing (1998).

Annex XII of Declaration of Dr. Anne Szarewski (Document D27 in Opposition to European Patent No. EP 0 911 029 B1), Larsson, K.S. and Machin, D., "Predictability of the safety of hormonal contraceptives from canine toxicological studies," in: *Safety requirements for contraceptive steroids*, Michael D., ed., Cambridge University Press, Oxford, UK, pp. 230-269 (1989).

Annex XIII of Declaration of Dr. Anne Szarewski (Document D27 in Opposition to European Patent No. EP 0 911 029 B1), Lumbiganon, P., "Depot-medroxyprogesterone acetete (DMPA) and cancer of the endometrium and ovary," *Contraception 49*:203-209, Butterworth-Heinemann (1994).

Annex XIV of Declaration of Dr. Anne Szarewski (Document D27 in Opposition to European Patent No. EP 0 911 029 B1), Rice, C.F., et al., "A comparison of the inhibition of ovulation achieved by desogestrel 75 µg and levnorgestrel 30 µg daily," *Human Reprod. 14*:982-985, Oxford University Press (1999).

Annex XV of Declaration of Dr. Anne Szarewski (Document D27 in Opposition to European Patent No. EP 0 911 029 B1), Rosenberg, M. and Waugh, M.S., "Causes and consequences of oral contraceptive noncompliance," *Am. J. Obstet. Gnyecol. 180*:S276-S279, Mosby, Inc. (1999).

Annex XVI of Declaration of Dr. Anne Szarewski (Document D27 in Opposition to European Patent No. EP 0 911 029 B1), Rosenberg, M.J., et al., "Use and Misuse of Oral Contraceptives: Risk Indicators for Poor Pill Taking and Discontinuation," *Contraception 51*:283-288, Elsevier Science Inc. (1995).

Annex XVII of Declaration of Dr. Anne Szarewski (Document D27 in Opposition to European Patent No. EP 0 911 029 B1), Rosenfield, A., et al., "The Food and Drug Administration and Medroxyprogesterone Acetate," *JAMA 249*:2922-2928, American Medical Association (1983).

Annex XVIII of Declaration of Dr. Anne Szarewski (Document D27 in Opposition to European Patent No. EP 0 911 029 B1), Szarewski, A., ed., "Figure 3.5 Oestrogen-dominant and progestogen-dominant pills," in: *Hormonal Contraception: A Women's Guide*, Macdonald Optima, pp. 45 (1991).

Annex XIX of Declaration of Dr. Anne Szarewski (Document D27 in Opposition to European Patent No. EP 0 911 029 B1), Szarewski, A. and Guillebaud, J., eds., "Which Pill will Suit me Best?," in: *Contraception, A User's Handbook*, Oxford University Press, pp. 43-72 (1994).

Annex XX of Declaration of Dr. Anne Szarewski (Document D27 in Opposition to European Patent No. EP 0 911 029 B1), Wilkinson, C. and Szarewski, A., eds., "Management of Breakthrough Bleeding," in: *Contraceptive Dilemmas*, Altman Publishing, St. Albans, England, pp. 4-7 (2003).

Annex XXI of Declaration of Dr. Anne Szarewski, (Document D27 in Opposition to European Patent No. EP 0 911 029 B1), WHO Collaborative Study Group, "Depot-Medroxyprogesterone Acetate (DMPA) and Risk of Endometrial Cancer," *Int. J. Cancer 49*:186-190, Wiley-Liss, Inc. (1991).

Annex XXII of Declaration of Dr. Anne Szarewski (Document D27 in Opposition to European Patent No. EP 0 911 029 B1), WHO Collaborative Study Group, "Breast cancer and depot-medroxyprogesterone acetate: a multinational study," *Lancet 338*:833-838, Lancet Publishing Company (1991).

European Opposition Document D28, SEA-301, Summary Statistics: Observed Total Number of Days of Unscheduled Bleeding and/or Spotting by Cycle, cited in the Opposition to European Patent No. 0 911 029 B1.

European Opposition Document D29, Letter from U.S. FDA to Barr Research, Inc., undated and redacted, cited in the Opposition to European Patent No. 0 911 029 B1.

European Opposition Document D30, European Patent No. 0 253 607 A1, published Jan. 20, 1988, cited in the Opposition to European Patent No. 0 911 029 B1.

European Opposition Document D31, Publicly available Food and Drug Administration papers relating to marketing authorization for Seasonale®, 347 pages, cited in the Opposition to Patent No. 0 911 029 B1 (publicly available Mar. 2004).

European Opposition Document D32, Facts About Seasonale®, 1 page, Barr Laboratories, Inc., available online at www.seasonale.com, cited in the Opposition to European Patent No. 0 911 029 B1.

European Opposition Document D33, Seasonale®, Product Brochure, 15 pages, available online at www.seasonale.com, cited in the Opposition to European Patent No. 0 911 029 B1.

European Opposition Document D34, Seasonale , Product Description and Information, Duramed Pharmaceuticals, Inc., 39 pages (Sep. 2003), cited in the Opposition to European Patent No. 0 911 029 B1.

Notice of Paragraph IV Certification letter on behalf of Watson Laboratories, Inc., from Barry S. White of Frommer Lawrence & Haug LLP to Bruce L. Downey of Barr Laboratories, Inc., 17 pages (Jun. 2004).

Letter from Andreas Görlich to Barr Laboratories, Inc., entitled "Tablets against pregnancy 'Seasonale'," 3 pages (Jun. 2004).

Attachment 1, Letter from Andreas Görlich to Barr Laboratories, "Gynäkologische Sensation oder graue Theorie? Monatsblutung nur noch zweimal im Jahr—wie ist das möglich?," (Gesundheits-Magazin) Health Magazine, 1 page (1984).

English language translation of Attachment 1 to Letter from Andreas Görlich to Barr Laboratories, "Gynecological Sensation or Gray Theory? Menstration only twice a year—how is that possible?," Health Magazine (1984).

Attachment 2, Letter from Andreas Görlich to Barr Laboratories, "Zwei Monatsblutungen pro Jahr sind genug. Gefordert ist die sog. Distanz-Pille," Medical Tribune/Gyne, 1 page (1983).

Attachment 3, Letter from Andreas Görlich to Barr Laboratories, "Zwei Monatsblutungen pro Jahr Bind genugt!" Medical Tribune, Austrian Edition, and Medical Tribune, Swiss Edition, 2 pages (1984).

English language translation of Attachments 2 and 3, Letter from Andreas Görlich to Barr Laboratories, "Two "Menstrual Periods" Per Year Are Enough," Medical Tribune/Gyne (1983).

Attachment 4, Letter from Andreas Görlich to Barr Laboratories, "Frauenarzt fordert: Schafft die sinniosen Monatsblutungen ab!" Cosmopolitan 9:177, 1 page (1984).

English language translation of Attachment 4 to Letter from Andreas Görlich to Barr Laboratories, "Gynecologist issues challenge: away with senseless menstrual bleeding!," Cosmopolitan 9:177 (1984).

Fernandez, E., et al., "Oral contraceptives and colorectal cancer risk: a meta-analysis," *Brit. J. Canc. 84*:722-727, Cancer Research Campaign (2001).

Garraway, W.M., et al., "Limb Fractures in a Defined Population. I. Frequency and Distribution," *Mayo Clin. Proc. 54*:701-707, Mayo Clinic (1979).

Gusberg, S.B. and Hall, R.E., "Precursors of Corpus Cancer. III. The Appearance of Cancer of the Endometrium in Estrogenically Conditioned Patients," *J. Obstet. Gynecol. 17*:397-412, Paul B. Hoeber, Inc. (1961).

Hipkin, L., Col., "The Induction of Amenorrhoea," *J.R. Army Med. Corps* 138:15-18, Royal Army Medical Corps (1992).

Holt, V., et al., "Body Weight and Risk of Oral Contraceptive Failure," *Obstet. Gynecol.* 99:820-827, American College of Obstetricians and Gynecologists (May 2002).

Kay, C.R. and Wingrave, S.J., "Oral Contraceptives and Rheumatoid Arthritis," *Lancet 1*:1437, Lancet Publishing Group (1983).

Koetsawang, S., et al., "A Randomized, Double-Blind Study of Six Combined Oral Contraceptives," *Contraception* 25:231-241, Elsevier (1982).

Kudrow, L., "The Relationship of Headache Frequency to Hormone Use in Migraine," *Headache* 15:36-40, Blackwell Science (1975).

Kuhl, H., "Comparative Pharmacology of Newer Progestogens," *Drugs* 51:189-215, ADIS International Ltd. (1996).

Linos, A., et al., "Rheumatoid Arthritis and Oral Contraceptives," *Lancet 1*:871, The Lancet Publishing Group (1978).

Lundeen, S.G., et al., "Rat uterine complement C3 expression as a model for progesterone receptor modulators: characterization of the new progestin trimegestone," *J. Steroid Biochem. & Molec. Biol.* 78:137-143, Elsevier Science Ltd. (2001).

MacDonald, N.E. and Brunham, R., "The Effects of Undetected and Untreated Sexually Transmitted Diseases: Pelvic Inflammatory Disease and Ectopic Pregnancy in Canada," *Canadian J. Human Sexuality* 6:161-170, Sieccan (1997).

"Medical Management of Endometriosis," *ACOG Practice Bulletin*, No. 11, pp. 1-14, American College of Obstetricians and Gynecologists (1999).

Philibert D., et al., "The Pharmacological profile of a novel norpregnane progestin (trimegestone)," *Gynecol. Endocrinol.* 13:316-326, Parthenon Publishing (1999).

"Premenstrual Dysphoric Disorder," in: *Diagnostic and Statistical Manual of Mental Disorders*, American Psychiatric Association, Washington, DC, pp. 715-718 (1994).

Report of a WHO Scientific Group, "8. Risks, with Particular Reference to Neoplasia, of Therapeutic Estrogens and Progestins Given to Peri- and Postmenopausal Women," in: *Research on the menopause*, World Health Organization, Geneva, Switzerland, pp. 52-69 (1981).

Rittmaster, R.S., "Hirsutism," *Lancet 349*:191-195, Lancet Publishing Group (1997).

Rosenberg, M.J. and Waugh, M.S., "Oral contraceptive discontinuation: A prospective evaluation of frequency and reasons," *Am. J. Obstet. Gynecol.* 179:577-582, Mosby, Inc. (1998).

Sheth, A., et al., "A Randomized, Double-Blind Study of Two Combined and Two Progestogen-Only Oral Contraceptives," *Contraception* 25:243-252, Elsevier (1982).

Steiner, M., "Premenstrual Syndromes," *Annu. Rev. Med.* 48:447-455, Annual Reviews Inc. (1997).

Sulak, P.J., et al., "Hormone Withdrawal Symptoms in Oral Contraceptive Users," *Obstet. Gynecol.* 95:261-266, Lippincott, Williams & Wilkins (2000).

Sulak, P.J., et al., "Acceptance of altering the standard 21-day/7-day oral contraceptive regimen to delay menses and reduce hormone withdrawal symptoms," *Am. J. Obstet. Gynecol.* 186:1142-1149, Mosby, Inc. (Jun. 2002).

Weström, L. and Märdh, P.-A., "Chap. 49. Acute pelvic inflammatory disease (PID)," in: *Sexually Transmitted Diseases*, 2nd Ed, Holmes, K.K., et al., eds., McGraw-Hill, Inc., New York, NY, pp. 593-613 (1990).

Whitty, C.W.M., et al., "The Effect of Oral Contraceptives on Migraine," *Lancet* 1:856-859, Lancet Publishing Company (1966).

Wysocki, S., et al., "Hormonal Contraceptives: Extending the Benefits," *Am. J. Nurse Pract.* 6:19-29, American College of Nurse Practitioners (Nov./Dec. 2002).

Co-Pending U.S. Appl. No. 10/892,404, Bell et al., filed Jul. 16, 2004.

Anderson, F.D., "The Safety and Efficacy of Seasonale, a Novel 91-Day Extended Oral Contraceptive Regimen," Abstract, *Obstet. Gynecol.* 99(4):26S, Lippincott Williams & Wilkins, Baltimore, MD (Apr. 2002).

"Seasonale," *Medical Letter on Drugs and Therapeutics*, vol. 46, issue 1175, p. 9, The Medical Letter, Inc., New Rochelle, NY (Feb. 2004).

Supplemental European Search Report for EP Patent Appl. No. 04760680, European Patent Office, Munich, Germany, mailed Jan. 22, 2009.

*Duramed Pharmaceuticals, Inc. v. Sandoz Inc.*, Civil Docket Case #: 3:07-cv-05940-MLC-TJB, U.S. District Court, District of New Jersey (Trenton), Filed on Dec. 13, 2007, 7 pages.

*Duramed Pharmaceuticals, Inc. v. Sandoz Inc., et al.*, Civil Docket Case #: 3:07-cv-05940-MLC-TJB, U.S. District Court, District of New Jersey (Trenton), "*Defendant Sandoz Inc. 's Amended Answer, Affirmative Defenses and Counterclaims to Plaintiff's Complaint*," Filed on Sep. 25, 2008, 14 pages.

*Duramed Pharmaceuticals, Inc. v. Watson Pharma, Inc. et al.*, Civil Docket Case #: 3:07-cv-05941-MLC-TJB, U.S. District Court, District of New Jersey (Trenton), Filed on Dec. 13, 2007, Terminated on Mar. 24, 2008, 5 pages.

*Duramed Pharmaceuticals, Inc. v. Watson Pharma, Inc., et al.*, Civil Docket Case #: 3:07-cv-05941-MLC-TJB, U.S. District Court, District of New Jersey (Trenton), "*Answer and Counterclaims of Defendants/Counterclaim-Plaintiffs Watson Pharma, Inc., Watson Laboratories, Inc., and Watson Pharmaceuticals, Inc.*," Filed on Mar. 3, 2008, 22 pages.

*Duramed Pharmaceuticals, Inc. v. Watson Laboratories, Inc. et al.*, Civil Docket Case #: 3:08-cv-00116-LRH-RAM, U.S. District Court, District of Nevada (Reno), Filed on Mar. 6, 2008, 20 pages.

*Duramed Pharmaceuticals, Inc. v. Watson Laboratories, Inc.*, Civil Docket Case #: 3:08-cv-00116 (LRH-RAM), U.S. District Court, District of Nevada (Reno), "*First Amended Answer, Affirmative Defenses and Counterclaims of Defendant Watson Laboratories, Inc.*," Filed on Dec. 19, 2008, 12 pages.

European Opposition Document, Appellant's Grounds of Appeal, with Main Request and First, Second, Third, Fourth, Fifth and Sixth Auxiliary Requests; 37 pages; submitted by Patentee in the Opposition to European Patent No. 0 911 029 B1 (Nov. 2004).

European Opposition Document D35, Declaration by Alan H. DeCherney, M.D., 6 pages, submitted with Appellant's Grounds of Appeal in the Opposition to European Patent No. 0 911 029 B1 (Nov. 2004).

Exhibit A of Declaration by Alan H. DeCherney, M.D. (European Opposition Document D35), *Curriculum Vitae*, Alan Hersh DeCherney, M.D., 54 pages, Dec. 2003, submitted with Appellant's Grounds of Appeal in the Opposition to European Patent No. 0 911 029 B1.

European Opposition Document D36, "Coolest Inventions 2003," *Time Magazine*, issue of Nov. 17, 2003, 26 pages, submitted with Appellant's Grounds of Appeal in the Opposition to European Patent No. 0 911 029 B1.

Sulak, P.J., "Should your patient be on extended-use OCs?" *Contemporary OB/GYN* 48:35-46, Thomson Medical Economics (Sep. 2003).

Docket Sheet for *Duramed Pharmaceuticals, Inc. v. Sandoz Inc.*, Civil Docket Case No. 3:07-CV-05940, U.S. District Court, District of New Jersey (Trenton), most recent entry date of Feb. 23, 2010, 24 pages.

Docket Sheet for *Teva Women's Health, Inc. v. Lupin, Ltd.* et al, Civil Docket Case No. 3:09-CV-05112, U.S. District Court, District of New Jersey (Trenton), most recent entry date of Mar. 22, 2010, 7 pages.

Docket Sheet for *Duramed Pharmaceuticals, Inc. v. Watson Laboratories, Inc.* et al, Civil Docket Case No. 3:08-CV-00116, U.S. District Court, District of Nevada (Reno), most recent entry date of Apr. 21, 2010, 60 pages.

"Order" in *Duramed Pharmaceuticals, Inc. v. Watson Laboratories, Inc.* et al, Civil Docket Case No. 3:08-CV-00116, U.S. District Court, District of Nevada (Reno), filed Mar. 31, 2010, 11 pages.

Docket Sheet for *Teva Women's Health, Inc. v. Lupin, Ltd.* et al, Civil Docket Case No. 2:10-CV-00603, U.S. District Court, District of New Jersey (Newark), most recent entry date of Apr. 12, 2010, 6 pages.

"*Answer and Counterclaims of Lupin Pharmaceuticals, Inc. And Lupin, Ltd.*" in *Teva Women's Health, Inc. v. Lupin, Ltd.* et al, Civil Docket Case No. 2:10-CV00603, U.S. District Court, District of New Jersey (Newark), filed Mar. 19, 2010, 13 pages.

Docket Sheet for *Teva Women's Health, Inc.* v. *Mylan Pharmaceuticals, Inc.* et al, Civil Docket Case No. 2:10-CV-01235, U.S. District Court, District of New Jersey (Newark), most recent entry date of Apr. 28, 2010, 4 pages.

Docket Sheet for *Teva Women's Health, Inc.* v. *Lupin, Ltd.* et al, Civil Docket Case No. 2:10-CV-00080, U.S. District Court, District of New Jersey (Newark), most recent entry date of Apr. 30, 2010, 11 pages.

Docket Sheet for *Watson Laboratories, Inc.* v. *Teva Women's Health, Inc.*, Civil Docket Case No. 3:10-CV-00115, U.S. District Court, District of Nevada (Reno) most recent entry date of Mar. 31, 2010, 3 pages.

"*Complaint for Declaratory Judgment of Patent Invalidity and Non-Infringement*" in *Watson Laboratories, Inc.* v. *Teva Women's Health, Inc.*, Civil Docket Case No. 3:10-CV-00115, U.S. District Court, District of Nevada (Reno), filed Feb. 25, 2010, 8 pages.

Docket Sheet for *Teva Women's Health, Inc.* v. *Mylan Pharmaceuticals, Inc.* et al, Civil Docket Case No. 2:10-CV-01234, U.S. District Court, District of New Jersey (Newark), most recent entry date of Mar. 15, 2010, 3 pages.

* cited by examiner

METHODS OF HORMONAL TREATMENT UTILIZING EXTENDED CYCLE CONTRACEPTIVE REGIMENS

CROSS-REFERENCE TO RELATED APPLICATIONS

This application claims the benefit, under 35 U.S.C. §119(e), of the earlier filing dates of U.S. Provisional Application No. 60/467,172, filed on May 2, 2003, and U.S. Provisional Application No. 60/524,081, filed on Nov. 24, 2003. The contents of each of these applications are incorporated herein by reference in their entirety.

BACKGROUND OF THE INVENTION

1. Field of the Invention

The present invention relates to methods of hormonal treatment involving extended administration of estrogen and progestin.

2. Related Art

The ovarian/menstrual cycle is a complex event characterized by an estrogen rich follicular phase and, after ovulation, a progesterone rich luteal phase. Each phase has a duration of approximately 14 days resulting in an intermenstrual interval of about 28 days. The endometrial tissue responds to the changes in hormonal milieu.

The onset of menstruation is generally considered to be the beginning of a new menstrual cycle and is generally counted as Day 1. During a span of about 5 to 7 days, the superficial layers of the endometrium, which grew and developed during the antecedent ovarian/menstrual cycle, are sloughed because demise of the corpus luteum in the non-fertile menstrual cycle is associated with a loss of progesterone secretion. Ovarian follicular maturation occurs progressively resulting in a rise in the circulating levels of estrogen, which in turn leads to new endometrial proliferation.

The dominant ovarian follicle undergoes ovulation at mid-cycle, generally between menstrual cycle days 12 to 16 and is converted from a predominantly estrogen source to a predominantly progesterone source (the corpus luteum). The increasing level of progesterone in the blood converts the proliferative endometrium to a secretory phase in which the tissue proliferation has promptly abated, leading to the formation of endometrial glands or organs. When the ovulated oocyte is viably fertilized and continues its progressive embryonic cleavage, the secretory endometrium and the conceptus can interact to bring about implantation (nidation), beginning about 6 to 8 days after fertilization.

If an ongoing pregnancy is to be established via implantation, the embryo will attach and burrow into the secretory endometrium and begin to produce human chorionic gonadotropin (HCG). The HCG in turn stimulates extended corpus luteum function, i.e., the progesterone production remains elevated, and menses does not occur in the fertile menstrual cycle. Pregnancy is then established.

In the non-fertile menstrual cycle, the waning level of progesterone in the blood causes the endometrial tissue to be sloughed. This starts a subsequent menstrual cycle.

Because endometrial proliferation serves to prepare the uterus for an impending pregnancy, manipulation of hormones and of the uterine environment can provide contraception. For example, estrogens are known to decrease follicle stimulating hormone secretion by feedback inhibition. Under certain circumstances, estrogens can also inhibit luteinizing hormone secretion, once again by negative feedback. Under normal circumstances, the spike of circulating estrogen found just prior to ovulation induces the surge of gonadotropic hormones that occurs just prior to and resulting in ovulation. High doses of estrogen immediately post-coitally also can prevent conception probably due to interference with implantation.

Progestins can also provide contraception. Endogenous progesterone after estrogen is responsible for the progestational changes of the endometrium and the cyclic changes of cells and tissue in the cervix and the vagina. Administration of progestin makes the cervical mucus thick, tenacious and cellular, which is believed to impede spermatozoal transport. Administration of progestin also inhibits luteinizing hormone secretion and blocks ovulation in humans.

The most prevalent form of oral contraception is a pill that combines both an estrogen and a progestin, a so-called combined oral contraceptive preparation. Alternatively, there are contraceptive preparations that comprise progestin only. However, the progestin-only preparations have a more varied spectrum of side effects than do the combined preparations, especially more breakthrough bleeding. As a result, the combined preparations are the preferred oral contraceptives in use today (Sheth et al., *Contraception* 25:243 (1982)).

Whereas the conventional 21 day pill packs with a 7 day "pill free" or placebo interval worked well when oral contraceptives were of higher dosage, as the doses have come down, for both the estrogen and progestin components, bleeding problems have increased in frequency, especially in the early months of oral contraceptive use, but even persistently so in some patients.

There exists a need for contraceptives that reduce bleeding problems and/or have additional benefits for women.

SUMMARY OF THE INVENTION

The present invention provides an extended estrogen/progestin regimen in which a female is administered a combined dosage form of estrogen and progestin for more than 50 consecutive days, in which the daily amounts of estrogen and progestin are equivalent to about 5 µg (micrograms) to about 50 µg of ethinyl estradiol and equivalent to about 0.01 mg (milligrams) to about 1.5 mg of levonorgestrel, respectively. This extended cycle regimen can be administered to a female to provide a number of non-contraceptive benefits, as well as contraceptive benefits.

Thus, the present invention is directed to a method of reducing breakthrough bleeding in a female in need thereof, the method comprising administering to the female the extended cycle regimen.

The invention is directed to a method of treating a menstrual bleeding disorder in a female in need thereof, the method comprising administering to the female the extended cycle regimen.

The invention is directed to a method of treating a symptom associated with an ovarian cyst, uterine leiomyoma (fibroid tumor), or Polycystic Ovarian Syndrome in a female in need thereof, the method comprising administering to the female the extended cycle regimen.

The invention is directed to a method of treating hirsutism in a female in need thereof, the method comprising administering to the female the extended cycle regimen.

The invention is directed to a method of treating a menstrual disorder in a female in need thereof, the method comprising administering to the female the extended cycle regimen. In some aspects, the invention is directed to a method of treating the menstrual disorder mettelschmerz.

The invention is directed to a method of treating acne in a female in need thereof, the method comprising administering to the female the extended cycle regimen.

The invention is directed to a method of reducing risk of ovarian cancer in a female in need thereof, the method comprising administering to the female the extended cycle regimen.

The invention is directed to a method of treating benign breast disease in a female in need thereof, the method comprising administering to the female the extended cycle regimen.

The invention is directed to a method of reducing risk of colorectal cancer in a female in need thereof, the method comprising administering to the female the extended cycle regimen.

The invention is directed to a method of treating an infection in a female in need thereof, the method comprising administering to the female the extended cycle regimen.

The invention is directed to a method of treating temporomandibular disorder in a female in need thereof, the method comprising administering to the female the extended cycle regimen.

The invention is directed to a method of treating a catamenial symptom in a female in need thereof, the method comprising administering to the female the extended cycle regimen.

The invention is directed to a method of treating a non-menstrual related headache in a female in need thereof, the method comprising administering to the female the extended cycle regimen.

The invention is directed to a method of treating non-menstrual related nausea in a female in need thereof, the method comprising administering to the female the extended cycle regimen.

The invention is directed to a method of treating non-menstrual related depression in a female in need thereof, the method comprising administering to the female the extended cycle regimen.

The invention is directed to a method of increasing contraceptive effectiveness in a higher weight female in need thereof, the method comprising administering to the female the extended cycle regimen.

The invention is directed to a method of treating a perimenopausal symptom in a female in need thereof, the method comprising administering to the female the extended cycle regimen.

The invention is directed to a method of treating hypoestrogenism in a female in need thereof, the method comprising administering to the female the extended cycle regimen.

The invention is directed to a method of treating a menopausal disorder in a female in need thereof, the method comprising administering to the female the extended cycle regimen.

The invention is directed to a method for treating a condition resulting from menopausal estrogen decline in a menopausal female, the method comprising administering to the female the extended cycle regimen.

The invention is directed to a method of maintaining bone density or preventing loss of bone density in a female in need thereof, the method comprising administering to the female the extended cycle regimen. In these aspects, vitamin D and/or calcium are optionally administered in combination with estrogen and progestin in the extended cycle regimen.

The invention is directed to a method of treating a female in need of hormone replacement therapy, the method comprising administering to the female the extended cycle regimen.

The invention is directed to a method of increasing fertility in a female in need thereof, the method comprising administering to the female the extended cycle regimen, followed by administration of an agent to induce ovulation in the female.

The invention is further directed to each of the methods provided above, wherein the combination of estrogen and progestin that is administered to the female for a period of more than 50 consecutive days is followed by a hormone-free period of about 2 to about 10 days, wherein neither estrogen nor progestin is administered to the female during the hormone-free period.

The invention is further directed to each of the methods provided above, wherein the combination of estrogen and progestin is administered for a period of 60 to 110 consecutive days, for a period of 80-90 consecutive days, for a period of about one year, for a period of more than one year but less than two years, for a period of two years, for a period of more than two years, or continuously.

The invention is also further directed to each of the methods provided above, wherein the combination of estrogen and progestin is administered for a period of 60 to 110 consecutive days, followed by a hormone-free period of about 2 to about 10 days, wherein neither estrogen nor progestin is administered to the female during the hormone-free period.

The invention is further directed to each of the methods provided above, wherein the hormone-free period is achieved by administering a hormone-free placebo.

The invention is further directed to each of the methods provided above, wherein the combination of estrogen and progestin is administered for at least 84 consecutive days.

The invention is further directed to each of the methods provided above, wherein the daily amount of estrogen is equivalent to about 10 µg to about 30 µg of ethinyl estradiol, and the daily amount of progestin is equivalent to about 0.05 mg to about 0.20 mg of levonorgestrel.

The invention is also directed to each of the methods listed above, wherein the female is a perimenopausal female or a menopausal female.

DETAILED DESCRIPTION OF THE INVENTION

Figure 1:
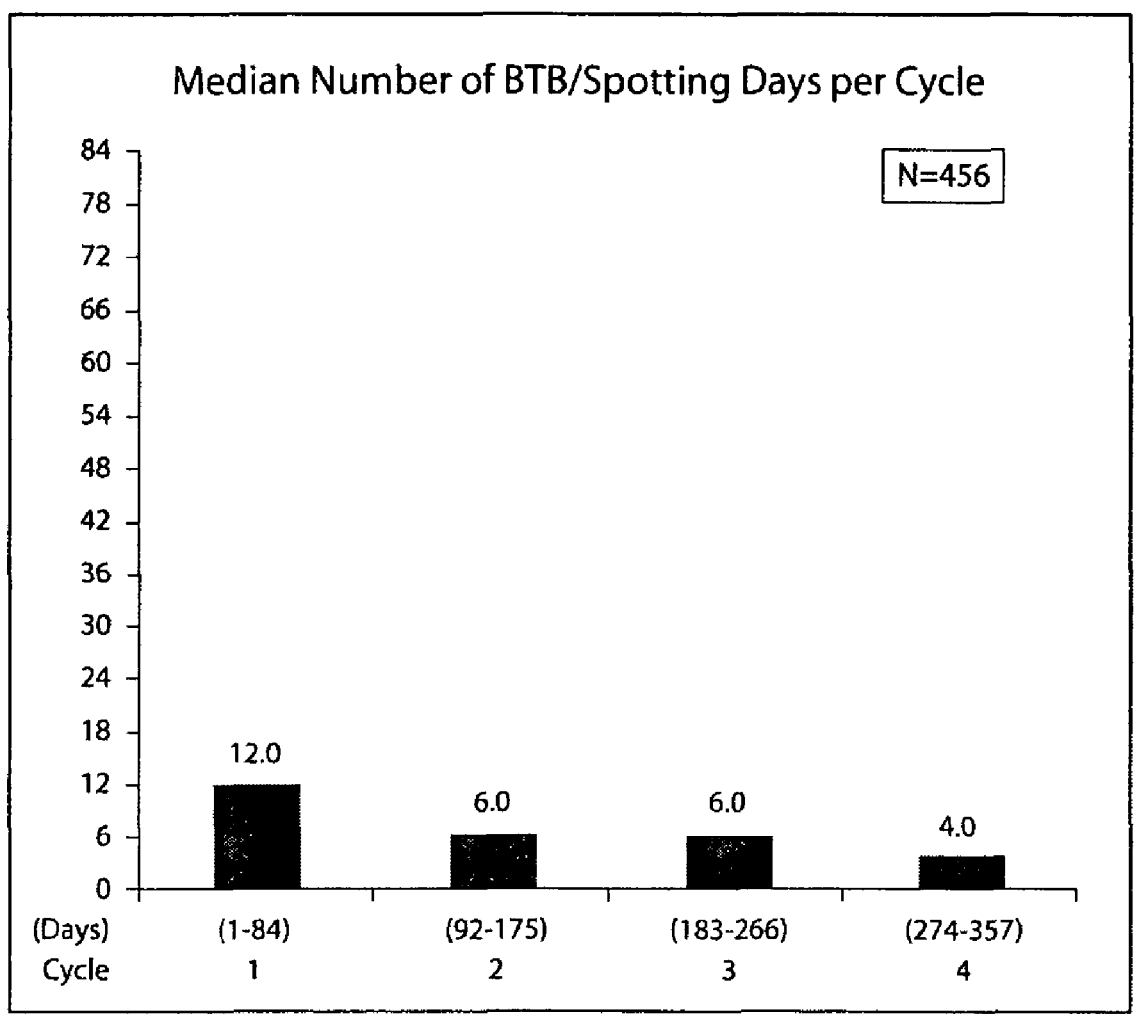
FIG. 1 shows the median number of days of breakthrough bleeding/spotting by cycle in patients receiving the 91-day extended cycle regimen in the clinical study described in Example 1.

The present invention provides extended estrogen/progestin regimens that are useful in the treatment of a variety of conditions and disorders occurring in females of child-bearing age, in peri-menopausal females, and/or in menopausal females, as well as for contraception. U.S. application Ser. No. 60/467,172, filed May 2, 2003, relates to the administration of extended estrogen/progestin regimens as a method of providing contraceptive and non-contraceptive benefits. U.S. Appl. No. 60/467,172 is fully incorporated by reference herein in its entirety.

Extended Cycle Regimens

In accordance with the present invention, a female is administered an "extended cycle regimen," i.e., a combined dosage form of estrogen and progestin (or progestogen) for more than 50 consecutive days, for greater than 50 consecutive days, or for at least 50 consecutive days, in which the daily dosage amount of estrogen can be equivalent to about 5 µg to about 50 µg of ethinyl estradiol and the daily dosage amount of progestin can be equivalent to about 0.01 mg to about 1.5 mg of levonorgestrel.

In some aspects of the invention, the combined dosage form of estrogen and progestin is administered for about 60 to about 110 consecutive days, or the combined dosage form is administered for about 80 to about 90 consecutive days. In other aspects of the invention, the period of administration can be about one year, more than one year but less than two years, two years, or more than two years. In some aspects of the invention, the period of administration is continuous.

In the extended cycle regimen, the combined dosage form of estrogen and progestin can be administered monophasically, biphasically, triphasically, or multiphasically. As used herein, "monophasic" refers to the continuous use of one particular dose of estrogen and progestin during the period of administration of the combined dosage form of estrogen and progestin. "Biphasic" refers to administration of a first continuous dose of estrogen and progestin during a first portion of the period of administration of the combined dosage form of estrogen and progestin, with administration of a second continuous dose of estrogen and progestin during the second portion of the period of administration of the combined dosage form. "Triphasic" refers to administration of first, second, and third continuous doses of estrogen and progestin during the first, second, and third portions, respectively, of the period of administration of the combined dosage form of estrogen and progestin. "Multiphasic" refers to administration of four or more continuous doses of estrogen and progestin during the first, second, third, and fourth or more portions, respectively, of the period of administration of the combined dosage form of estrogen and progestin.

In the extended cycle regimen of the invention, the period of administration of the combined dosage form of estrogen and progestin is optionally followed by a period of about 2 to about 10 days during which neither estrogen nor progestin is administered ("hormone-free period"). In other aspects of the invention, the hormone-free period is about 5 to about 8 days. In yet other aspects of the invention, the hormone-free period is about 7 days.

In some aspects of the invention, the hormone-free period is achieved by administering a hormone-free placebo during that period.

For example, on a schedule of 84 days of administration followed by a hormone-free period of 7 days, there are only four treatments and menstrual cycles per year. As another example, on a schedule of 175 days of administration followed by a hormone-free period of 7 days, there are only two treatments and menstrual cycles per year.

Methods of Treatment

The extended cycle regimen disclosed herein can be used as a method of female contraception. Thus, the invention is directed to a method of providing contraception to a female in need thereof by administering to the female the extended cycle regimen disclosed herein. The female can be, for example, of childbearing age or peri-menopausal.

However, the extended cycle regimen is also useful as a method of treating a variety of conditions and disorders in females, including peri-menopausal and menopausal females. Thus, the extended cycle regimen can be used as a method of providing contraception to a female for the treatment of a condition or disorder, or as a method of providing contraception and treating a condition or disorder in a female. Such conditions and disorders are described below and include, but are not limited to: breakthrough bleeding; irregular withdrawal bleeding; menstrual bleeding disorders; symptoms associated with an ovarian cyst, uterine leiomyoma (fibroid tumor), and/or Polycystic Ovarian Syndrome; hirsutism; iron deficiency anemia; menstrual disorders; acne; endometriosis; endometrial cancer; ovarian cancer; benign breast disease; infections; ectopic pregnancy; temporomandibular disorder; catamenial symptoms; non-menstrual related headache, nausea, and/or depression; peri-menopausal symptoms; hypoestrogenism; menopausal disorders; and loss of bone density.

The invention, therefore, is directed to a method of providing contraception to a female for the treatment of a condition or disorder, wherein the female is in need of treatment for the condition or disorder, by administering to the female the extended cycle regimen disclosed herein. The female can be, for example, of childbearing age, peri-menopausal, or menopausal.

The invention is also directed to a method of providing contraception and treating a condition or disorder in a female, wherein the female is in need of both contraception and treatment of the condition or disorder, by administering to the female the extended cycle regimen disclosed herein. The female can be, for example, of childbearing age or peri-menopausal.

The extended cycle regimen disclosed herein can include administration to a female beginning at Day 1 of a menstrual cycle that is defined as beginning at the first day of menstrual flow. Alternatively, the extended cycle regimen disclosed herein can also include administration to a female beginning at Day 1 of a menstrual cycle that is defined as beginning at the day after the ending of the menstrual flow. Alternatively, the extended cycle regimen disclosed herein also can include administration to a female beginning at Day 1 of a menstrual cycle that is defined as beginning at any day within the menstrual cycle.

As used herein, "female" refers to any animal classified as a mammal, including humans and non-humans, such as, but not limited to, domestic and farm animals, zoo animals, sports animals, and pets.

"Peri-menopausal female" refers to a woman who has not yet definitely arrived at menopause but who is experiencing symptoms associated with menopause. "Peri-menopause" means "about or around the time of menopause." It encompasses the years preceding the last menstrual period during which ovarian function declines and ultimately ceases and can include the presence of symptoms and irregular cycles. "Menopausal female" refers to a woman who has definitely arrived at menopause and may be experiencing symptoms associated with menopause. Menopause or post-menopause is the permanent cessation of menstruation after the loss of ovarian activity and is generally defined clinically as the absence of menstruation for about one year. Menopause may occur naturally in a woman or it may be artificially induced, e.g., through surgical or chemical means. For example, removal of the ovaries, which can occur, e.g., through hysterectomy, frequently leads to symptoms associated with menopause ("surgical menopause").

The terms "treat" and "treatment" refer to both therapeutic treatment and prophylactic or preventative measures, wherein the object is to prevent or slow down (lessen) an undesired physiological condition, disorder or disease, or obtain beneficial or desired clinical results. For purposes of this invention, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state, remission (whether partial or total), whether detectable or undetectable; or enhancement or improvement of condition, disorder or disease. Treatment includes eliciting a clinically significant response, without excessive levels of side effects. Treatment also includes prolonging survival as compared to expected survival if not receiving treatment.

The term "continuous" or "consecutive" in reference to "administration" means that the frequency of administration is at least once daily. Note, however, that the frequency of administration can be greater than once daily and still be "continuous," e.g., twice or even three times daily, as long as the dosage levels as specified herein are not exceeded.

The term "dosage level" means the total amount of estrogen or progestin administered per day. Thus, for example, "continuous administration" of a progestin to a woman at a "dosage level" of 30 μg means that the woman receives a total of 30 μg of progestin on a daily basis, whether the progestin is administered as a single 30 μg dose or, e.g., three separate 10 μg doses. A conventional means of continuously administering an estrogen or progestin is as a single daily oral dose at the prescribed dosage level.

When the period of continuous administration of estrogen and progestin, which in some aspects of the invention is 60 to 110 consecutive days, is followed by a hormone-free period of 2 to 10 days, the extended cycle regimen is characterized by a reduced incidence of breakthrough or unscheduled bleeding by about the fourth cycle. When the extended cycle regimen is administered on a schedule of, e.g., 84 days of administration of the estrogen and progestin, followed by a hormone-free period of, e.g., 7 days, the incidence of breakthrough bleeding decreases with continued use of the extended cycle regimen, so that by the fourth menstrual cycle (after about 274 days), it is comparable to that observed with the traditional 28-day regimen. Further continued use of the disclosed extended regimen can lead to even further reduction in the incidence of breakthrough bleeding. Thus, the present invention is directed to a method of reducing breakthrough bleeding in a female in need thereof by administering the extended cycle regimen disclosed herein to the female. For example, the female can be of childbearing age or peri-menopausal.

The invention is also directed to a method of providing contraception and reducing breakthrough bleeding in a female in need thereof by administering to the female the extended cycle regimen disclosed herein. For example, the female can be of childbearing age or peri-menopausal.

The invention is directed to a method of inducing regular, predictable withdrawal bleeding in a female in need thereof by administering to the female the extended cycle regimen disclosed herein. The female can be, but is not limited to, a female of childbearing age or a peri-menopausal female. Administration of the extended cycle regimen is useful in controlling menstrual cycles in a female by inducing regular, predictable withdrawal bleeding. By suppressing ovulation and delivering estrogen and progesterone in a programmed fashion, the extended cycle regimen can establish or restore synchrony to the endometrium. This is particularly useful in the treatment of heavy or intermenstrual bleeding. The resulting predictable timing and shorter duration of bleeding are especially advantageous to peri-menopausal women, who often experience irregular menstrual cycles.

The invention is also directed to a method of providing contraception and inducing regular, predictable withdrawal bleeding in a female in need thereof by administering to the female the extended cycle regimen disclosed herein. The female can be, for example, a female of childbearing age or a peri-menopausal female.

The invention is directed to a method of reducing frequency or delaying onset of a menstrual cycle in a female in need of delayed or reduced menstruation by administering to the female the extended cycle regimen disclosed herein. The female can be, but is not limited to, a female of childbearing age or a peri-menopausal female. Particular groups or subpopulations of women can benefit from reduced menstruation, such as women enlisted in the military and women athletes. Control of the menstrual cycle, or even induction of amenorrhea using the extended bridged cycle regimen, can be an advantage for women on active duty. The non-contraceptive benefits resulting from use of the extended cycle regimen, such as reduction in dysmenorrhea, premenstrual syndrome, menorrhagia, iron deficiency anemia, and ability to control timing of withdrawal bleeding, can be desirable and advantageous to women athletes as well.

The invention is also directed to a method of providing contraception and reducing frequency or delaying onset of a menstrual cycle in a female in need thereof by administering to the female the extended cycle regimen disclosed herein. The female can be, for example, a female of childbearing age or a peri-menopausal female.

The invention is directed to a method for minimizing uterine bleeding in a female in need thereof by administering to the female the extended cycle regimen disclosed herein. The female can be, but is not limited to, a female of childbearing age or a peri-menopausal female. By diminishing endometrial proliferation, administration of estrogen and progestin in the extended cycle regimen can reduce the volume and duration of menstrual flow. A female on the disclosed extended regimen experiences fewer total scheduled days of bleeding than a female on a traditional 28-day regimen, and experiences less blood loss, because the extended cycle regimen involves fewer stop/start transitions per year. The female to be treated can exhibit menorrhagia or abnormal uterine bleeding. Menorrhagia or abnormal uterine bleeding is often associated with conditions that include, but are not limited to, adenomyosis and uterine leiomyomas (uterine fibroids). As used herein, "abnormal uterine bleeding" refers to an abnormal duration of bleeding (i.e., greater than about 7 days of bleeding, or hypermenorrhea), abnormal amount of bleeding (i.e., greater than about 80 mL blood loss during menses, or menorrhagia), increased frequency of bleeding (i.e., less than about 22 days between menstrual cycles, or polymenorrhea), or any combinations thereof.

The invention is also directed to a method of providing contraception and minimizing uterine bleeding in a female in need thereof by administering to the female the extended cycle regimen disclosed herein. The female can be, for example, a female of childbearing age or a peri-menopausal female.

The invention is, moreover, directed to a method of treating a menstrual bleeding disorder in a female in need thereof by administering to the female the extended cycle regimen disclosed herein. The female can be, but is not limited to, a female of childbearing age or a peri-menopausal female.

The invention is also directed to a method of providing contraception and treating a menstrual bleeding disorder in a female in need thereof by administering to the female the extended cycle regimen disclosed herein. The female can be, for example, a female of childbearing age or a peri-menopausal female.

The invention is directed to a method of treating symptoms associated with ovarian cysts, uterine leiomyomas (fibroids), or Polycystic Ovarian Syndrome in a female in need thereof by administering to the female the extended cycle regimen disclosed herein. The female can be, for example, of childbearing age, peri-menopausal, or menopausal. The invention is also directed to a method of providing contraception and treating symptoms associated with ovarian cysts, uterine leiomyomas (fibroids), or Polycystic Ovarian Syndrome in a female in need thereof by administering to the female the extended cycle regimen disclosed herein. The female can be, for example, a female of childbearing age or peri-menopausal.

Ovarian cysts, uterine leiomyomas (fibroids), or Polycystic Ovarian Syndrome can cause symptoms including, but not limited to, pelvic pain, dysmenorrhea, abnormal uterine bleeding, acne, and hirsutism. In the invention, such symptoms can be treated by administration of the extended cycle regimen described herein.

Ovarian cysts arise from functional cysts that commonly occur around mid-cycle, when a follicle destined to become an egg fails to mature. Instead of leaving the ovary in a process known as ovulation, it remains inside, floating in a tiny sac of fluid. It is that sac that eventually forms into a cyst. Although rarely malignant, ovarian cysts lead to 200,000 hospitalizations in the United States each year. For some women, some studies have shown that the cysts develop cycle after cycle. Though ovarian cysts can sometimes be asymptomatic, they can also cause pain (constant pelvic pain, pain during intercourse, pain during pelvic movement, and/or pain before or after menses), abnormal bleeding (lengthened, shortened, irregular and/or absent menses), and/or abdominal bloating or distension.

Uterine fibroids are benign growths of uterine muscle that sometimes exist singly, but most often are multiple and range in size from microscopic to filling most of the lower abdominal cavity. Many women with fibroids have no symptoms at all. For those that do, the most common complaints are pressure symptoms and heavy, prolonged periods. There may be pressure in the pelvic region from the enlarged uterus, and the resulting symptoms are often related to where the fibroid is exerting pressure (e.g., increased urinary frequency, constipation or difficulty with bowel movements). The pressure can also cause backache, lower abdominal discomfort, and pain during and after intercourse. Fibroids can cause very heavy and prolonged periods, leading to iron-deficiency anemia, as well as painful periods (secondary dysmenorrhea). The presence of fibroids can also cause reproductive problems such as infertility, multiple miscarriages, premature labor, or labor complications.

The term "ovarian cyst" as used above represents more singular occurrences caused by the failure of an egg to mature. Polycystic Ovarian Syndrome (PCOS), in contrast, is due to an abnormal production of LH (luteinizing hormone) and FSH (follicle stimulating hormone) by the pituitary gland. An imbalance of these hormones stops egg production and increases production of androgens, with the ovaries producing higher levels of testosterone and estrogens. This results in ovaries "peppered" with empty egg follicles that become inflamed cysts, irregular or stopped periods (which in turn causes infertility), excess body hair growth, and acne on the face and body. PCOS often leads to obesity, diabetes and hypertension.

Polycystic Ovarian Syndrome is the cause of most cases of androgen-dependent hirsutism. See Rittmaster, R. S., *Lancet* 349:191-195 (1997). Hirsutism can be described as the growth of excessive hair in women on parts of the body where excessive hair is generally not present, e.g., on the back and chest. Most cases of hirsutism are androgen-dependent, i.e., result from a combination of increased androgen production by the body and increased skin sensitivity to androgens. Normally, small quantities of androgens are produced by the ovaries and the adrenal glands. However, in women suffering from Polycystic Ovarian Syndrome, androgen levels are elevated, which can lead to the development of androgen-dependent conditions such as, for example, pronounced forms of acne (e.g., acne papulopustulosa), androgenetic alopecia and mild forms of hirsutism. Oral contraceptives can suppress the ovarian production of androgens and are thus useful in the treatment of these androgen-dependent conditions.

Thus, the invention is also directed to a method of treating hirsutism in a female in need thereof, by administering to the female the extended cycle regimen disclosed herein. The female can be, for example, of childbearing age, peri-menopausal, or menopausal.

The invention is also directed to a method of providing contraception and treating hirsutism in a female in need thereof, by administering to the female the extended cycle regimen disclosed herein. The female can be, for example, a female of childbearing age or peri-menopausal.

The invention is further directed to a method of treating alopecia in a female in need thereof, by administering to the female the extended cycle regimen disclosed herein. The female can be, for example, of childbearing age, peri-menopausal, or menopausal. The invention is also directed to a method of providing contraception and treating alopecia in a female in need thereof, by administering to the female the extended cycle regimen disclosed herein. The female can be, for example, a female of childbearing age or peri-menopausal.

The invention is directed to a method of decreasing risk of iron deficiency anemia in a female in need thereof by administering to the female the extended cycle regimen disclosed herein. The female can be, but is not limited to, a female of childbearing age or a peri-menopausal female. The reduction in the volume and duration of menstrual flow that results from administration of the extended cycle regimen can lead to a reduction in the total loss of blood, thus improving the body's iron stores and reducing the morbidity associated with menorrhagia. This effect is particularly desirable in women with coagulation or bleeding disorders that include, but are not limited to, von Willebrand's disease, hemophilia, Factor XI deficiency, chronic anticoagulation, and thrombocytopenia.

The invention is also directed to a method of providing contraception and decreasing risk of iron deficiency anemia in a female in need thereof by administering to the female the extended cycle regimen disclosed herein. The female can be, for example, a female of childbearing age or a peri-menopausal female.

The invention is directed to a method of treating a menstrual disorder in a female in need thereof by administering to the female the extended cycle regimen disclosed herein. The female can be, but is not limited to, a female of childbearing age or a peri-menopausal female. Menstrual disorders include, but are not limited to, irregular cycles, dysmenorrhea (painful menstruation), mittelschmerz, and dysfunctional uterine bleeding, as well as premenstrual symptoms such as, but not limited to, those associated with premenstrual syndrome (PMS) or Premenstrual Dysphoric Disorder (PMDD).

The invention is also directed to a method of providing contraception and treating a menstrual disorder in a female in need thereof by administering to the female the extended cycle regimen disclosed herein. The female can be, for example, a female of childbearing age or a peri-menopausal female.

During the luteal phase of the menstrual cycle, as many as 75% of women with regular menstrual cycles experience some symptoms of premenstrual syndrome (PMS), a recurring, cyclical disorder involving behavioral, emotional, social and physical symptoms (Steiner et al., *Annu. Rev. Med.* 48:447-455 (1997)). Behavioral, emotional and social symptoms include, but are not limited to, irritability, mood swings, depression, hostility and social withdrawal. Physical symptoms include, but are not limited to, bloating, breast tenderness, myalgia, migraines or headaches, abdominal pain, and fatigue. True PMS only occurs during the luteal phase of the menstrual cycle, with a symptom-free period during the follicular phase. The etiology of PMS is still unknown.

A subgroup of women with PMS, about 2% to about 9%, exhibit symptoms that are primarily related to a severe mood disorder. In these women, the diagnosis of Premenstrual Dysphoric Disorder (PMDD), as defined in the Fourth edition of the Diagnostic and Statistical Manual of Mental Disorders (DSM-IV), can be applied (see "Premenstrual Dysphoric Disorder," in DSM-IV™: Diagnostic and Statistical Manual of Mental Disorders, $4^{th}$ Ed., American Psychiatric Association, Washington, D.C., pp. 715-718 (1994)). According to the DSM-IV, a woman with PMDD must have at least five premenstrual symptoms during the luteal phase, with at least one of the symptoms being an emotional or "core" symptom. The core symptoms must be irritability, anger, mood swings, tension or depression (and interfere with daily activities), and must be confirmed by a prospective daily rating for at least two cycles. Three to five percent of women with PMS report to have PMDD. There is also a subgroup of women who experience severe PMS, which accounts for about 20% of the PMS population. These women experience severe emotional symptoms that do not fall under the strict criteria of PMDD as defined in DSM-IV but require medical attention.

Suppression of ovulation that results from administration of the extended cycle regimen can also eliminate mid-cycle pain ("mittelschmerz") associated with rupture of the ovarian follicle. Additionally, suppression of ovulation and delivery of estrogen and progesterone in a regular, predictable schedule, which results from use of the extended cycle regimen can be beneficial in the treatment of other menstrual disorders such as heavy or intermenstrual bleeding. In some aspects of the invention, the female is, but not limited to, a peri-menopausal female.

The invention is directed to a method of treating acne in a female in need thereof by administering to the female the extended cycle regimen disclosed herein. The female can be, for example, of childbearing age, peri-menopausal, or menopausal. The extended cycle regimen can suppress gonadotropin and decrease ovarian and adrenal androgen production, resulting in an improvement in acne.

The invention is also directed to a method of providing contraception and treating acne in a female in need thereof by administering to the female the extended cycle regimen disclosed herein. The female can be, for example, a female of childbearing age or peri-menopausal.

The invention is directed to a method of treating endometriosis in a female in need thereof by administering to the female the extended cycle regimen disclosed herein. The female can be, but is not limited to, a female of childbearing age or a peri-menopausal female. The invention is also directed to a method of providing contraception and treating endometriosis in a female in need thereof by administering to the female the extended cycle regimen disclosed herein. The female can be, for example, a female of childbearing age or a peri-menopausal female.

In hormonal therapy of endometriosis, endometriotic tissue responds to adverse endocrine environments (low estrogen and/or high progestin concentration). Progestins produce marked atrophy of the endometrium and ectopic endometrial tissue and decrease intraperitoneal inflammation associated with endometriosis. The American College of Obstetrics and Gynecology stated that progestins, alone or in combination with estrogens as oral contraceptives, are an optimal choice for the management of endometriosis in women who desire contraception (American College of Obstetricians and Gynecologists, *ACOG Practice Bulletin No*. 11 (December 1999)). Since pain associated with endometriosis is often episodic and related to uterine bleeding, the use of the extended cycle regimen of the present invention is beneficial for treating endometriosis.

The invention is further directed to a method of reducing the risk of endometrial cancer in a female in need thereof by administering to the female the extended cycle regimen disclosed herein. The female can be, for example, of childbearing age, peri-menopausal, or menopausal. The invention is also directed to a method of providing contraception and reducing the risk of endometrial cancer in a female in need thereof by administering to the female the extended cycle regimen disclosed herein. The female can be, for example, a female of childbearing age or peri-menopausal.

The invention is directed to a method of reducing the risk of ovarian cancer in a female in need thereof by administering to the female the extended cycle regimen disclosed herein. The frequency of ovulation and thereby the frequency of ovarian stimulation can be reduced, suppressed, or eliminated by use of the extended cycle regimen. The female can be, for example, of childbearing age, peri-menopausal, or menopausal. The invention is also directed to a method of providing contraception and reducing the risk of ovarian cancer in a female in need thereof by administering to the female the extended cycle regimen disclosed herein. The female can be, for example, a female of childbearing age, peri-menopausal, or menopausal.

The invention is further directed to a method of treating benign breast disease, including, but not limited to, fibrocystic breast disease, in a female in need thereof by administering to the female the extended cycle regimen disclosed herein. The female can be, for example, of childbearing age or peri-menopausal. Roughly a third of all women between the ages of 30 and 50 will be diagnosed with fibrocystic breast disease or other benign breast conditions. Other terms for fibrocystic breast disease include benign breast disease and mammary dysplasia.

The invention is also directed to a method of providing contraception and treating benign breast disease in a female in need thereof by administering to the female the extended cycle regimen disclosed herein. The female can be, for example, a female of childbearing age or peri-menopausal.

The invention is directed to a method of reducing the risk of colorectal cancer in a female in need thereof by administering to the female the extended cycle regimen disclosed herein. The female can be, for example, of childbearing age, peri-menopausal, or menopausal. The extended cycle regimen of the present invention can protect against colorectal cancer as a result of changes in bile synthesis and secretion due to the female hormones in the regimen, which can lead to a reduced concentration of bile acids in the colon. It has also been observed that estrogen inhibits the growth of colon cancer cells in vitro, and estrogen receptors have been identified in normal and neoplastic colon epithelial cells. See Fernandez, E., et al., *British J. Cancer* 84:722-727 (2001). Thus, the extended cycle regimen is beneficial in the prevention or reduction in the occurrence of colorectal cancer.

The invention is also directed to a method of providing contraception and reducing the risk of colorectal cancer in a female in need thereof by administering to the female the extended cycle regimen disclosed herein. The female can be, for example, a female of childbearing age or peri-menopausal.

The invention is directed to a method of treating an infection in a female in need thereof by administering to the female the extended cycle regimen disclosed herein. The female can be, for example, of childbearing age, peri-menopausal, or menopausal. For example, sexually transmitted diseases (STDs) are infections caused by a pathogen such as a virus, bacterium, parasite, or fungus, that is spread from person to person through sexual contact. STDs can be painful, irritating, and even life-threatening. The extended cycle regimen can have a protective role against the development of some STDs because it stimulates the body to produce a thicker cervical mucous, which acts as a barrier to semen carrying bacteria that cause sexually transmitted diseases.

The invention is also directed to a method of providing contraception and treating an infection in a female in need thereof by administering to the female the extended cycle regimen disclosed herein. The female can be, but is not limited to, a female of childbearing age or peri-menopausal.

Pelvic Inflammatory Disease (PID) is a complication that can result from STD infections. PID is a serious syndrome of the female reproductive tract that results from the spread of infections (most often sexually transmitted infections such as *Chlamydia trachomatis* and *Nisseris gonnorrheoea*) from the vagina and endocervix to the uterus, fallopian tubes and ovaries. PID is commonly manifested as endometritis (infection of the lining of the uterus) or salpingitis (infection of the fallopian tubes), and less commonly as pelvic peritonitis and/or inflammation of contiguous structures. (MacDonald, N. E., and Bowie, W. R., *Canadian Communicable Disease Report* 21S4: 25-33 (1995); Westrom, L. and Mardh, P-A., *Sexually Transmitted Diseases*, $2^{nd}$ Ed., pages 593-613, New York: McGraw-Hill, 1990).

PID is a major cause of infertility and ectopic pregnancy. Ectopic pregnancy results from the implantation of a fertilized ovum in the fallopian tube or in the abdominal cavity and is thought to be caused by ciliary dysfunction within the fallopian tube resulting from prior tubal infection with *N. gonorrhoea* and/or *C. trachomatis*, which often results in loss of ciliated epithelial cells from the fallopian tubes. It has been estimated that prior tubal infection with STD agents causes about 50% of the cases of ectopic pregnancy. (MacDonald, N. E., and Brunham, R., *Canadian Journal of Human Sexuality* 6(2):161-170 (1997).)

The extended cycle regimen can have a protective role against the development of PID because it stimulates the body to produce thicker cervical mucous, which helps prevent semen carrying STD-causing bacteria from gaining access to the uterus and eventually causing PID and PID-related complications, such as ectopic pregnancy. Thus, the extended cycle regimen of the present invention is useful in the prevention or reduction in occurrence of sexually transmitted diseases, Pelvic Inflammatory Disease, and ectopic pregnancy. Accordingly, the invention is directed to a method of treating a sexually transmitted disease or Pelvic Inflammatory Disease in a female in need thereof by administering to the female the extended cycle regimen disclosed herein. The invention is also directed to a method of preventing ectopic pregnancy in a female in need thereof by administering to the female the extended cycle regimen disclosed herein. The female can be, but is not limited to, a female of childbearing age or a peri-menopausal female.

The invention is directed to a method of providing contraception and treating a sexually transmitted disease or Pelvic Inflammatory Disease in a female in need thereof by administering to the female the extended cycle regimen disclosed herein. The invention, moreover, is directed to a method of providing contraception and preventing ectopic pregnancy in a female in need thereof by administering to the female the extended cycle regimen disclosed herein. The female can be, but is not limited to, a female of childbearing age or a peri-menopausal female.

In addition, use of the extended cycle regimen, in comparison to the use of a conventional 28-day contraceptive regimen, can lead to a reduction in the reported occurrences of infection such as urinary tract infections, pharyngitis, upper respiratory tract infections, and sinusitus. Thus, the invention is further directed to a method of treating certain infections, such as urinary tract infections, pharyngitis, upper respiratory tract infections, and sinusitus, in a female in need thereof by administering to the female the extended cycle regimen disclosed herein. The female can be, for example, of childbearing age, peri-menopausal, or menopausal. The invention is also directed to a method of providing contraception and treating certain infections, such as urinary tract infections, pharyngitis, upper respiratory tract infections, and sinusitus, in a female in need thereof by administering to the female the extended cycle regimen disclosed herein. The female can be, for example, of childbearing age or peri-menopausal.

The invention is directed to a method of treating temporomandibular disorder in a female in need thereof by administering to the female the extended cycle regimen disclosed herein. The female can be, for example, of childbearing age, peri-menopausal, or menopausal. Temporomandibular disorders (TMD) are disorders of the jaw muscles, temporomandibular joints, and/or the nerves associated with chronic facial pain. The extended cycle regimen of the present invention is useful in the treatment of TMD. The invention is also directed to a method of providing contraception and treating temporomandibular disorder in a female in need thereof by administering to the female the extended cycle regimen disclosed herein. The female can be, for example, of childbearing age or peri-menopausal.

The invention is directed to a method of treating a catamenial symptom in a female in need thereof by administering to the female the extended cycle regimen disclosed herein. The female can be, for example, of childbearing age or peri-menopausal. Catamenial symptoms are those associated with conditions, disorders, or diseases that can worsen around the time of menses. Such conditions, disorders, or diseases include, but are not limited to, asthma, rheumatoid arthritis, migraine headaches, seizure disorders or epilepsy, multiple sclerosis, and diabetes. The invention is also directed to a method of providing contraception and treating a catamenial symptom in a female in need thereof by administering to the female the extended cycle regimen disclosed herein. The female can be, for example, of childbearing age or peri-menopausal.

Arthritis is a prevalent chronic condition in women. Hormonal factors can influence the frequency and severity of arthritis. In some women, arthritis symptoms such as joint stiffness, swelling and pain peak during the postovulatory phase of the menstrual cycle, and cyclic changes in local antibody release, white blood cell subpopulations and altered pain perception have been proposed as possible mechanisms (Case, A. M. and Reid, R. L., *Arch. Intern. Med.* 158:1405-1412 (1998)). Estrogen administered as a single agent, and as part of a combined oral contraceptive has been reported to benefit some women (Kay, C. R. and Wingrave, S. J., *Lancet* 1:1437 (1983); Linos, A., et al., *Lancet* 1:1871 (1978)). Thus, use of the extended cycle regimen is beneficial as a method of treating a catamenial symptom, such as, e.g., a symptom associated with rheumatoid arthritis, in a female in need thereof.

Approximately 60% of women with migraines report a relationship to menstruation (Case, A. M. and Reid, R. L., *Arch. Intern. Med.* 158:1405-1412 (1998)). Decreasing levels of estrogen during the late luteal phase of the menstrual cycle or abrupt withdrawal of estrogen as during the hormone-free period in women taking oral contraceptives are thought to trigger migraine attacks (Sulak P. J., et al., *Obstet. Gynecol* 95:261-266 (2000); Kudrow, L., *Headache* 15:36-49 (1975); Whitty, C. W. M., et al., *Lancet* 1:856-859 (1966)). Thus, use of the extended cycle regimen is beneficial as a method of treating a catamenial symptom in a female in need thereof, such as, e.g., a migraine headache, in a female.

Catamenial epilepsy refers to seizure disorders that occur or worsen around menstruation. It is believed to result from cyclic alterations in both ovarian hormone levels and drug metabolism (Case, A. M. and Reid, R. L., *Arch. Intern. Med.* 158:1405-1412 (1998)). Thus, use of the extended cycle regimen is beneficial as a method of treating a catamenial symptom such as, e.g., a symptom associated with epilepsy, in a female in need thereof.

The invention is directed to a method of treating headache or nausea unrelated to the menstrual cycle in a female in need thereof by administering to the female the extended cycle regimen disclosed herein. The female can be, for example, of childbearing age, peri-menopausal, or menopausal. Use of the extended cycle regimen, in comparison to the use of a conventional 28-day contraceptive regimen, can lead to a reduction in the reported occurrences of non-menstrual related headache and nausea. Thus, the disclosed extended cycle regimen can be used as a method of preventing or treating non-menstrual related headache and nausea. The invention is also directed to a method of providing contraception and treating headache or nausea unrelated to the menstrual cycle in a female in need thereof by administering to the female the extended cycle regimen disclosed herein. The female can be, for example, of childbearing age or peri-menopausal.

The invention is directed further to a method of treating depression unrelated to the menstrual cycle in a female in need thereof by administering to the female the extended cycle regimen disclosed herein. The female can be, for example, of childbearing age, peri-menopausal, or menopausal. "Depression" is a term that is often used to refer to different forms of depressive disorders and includes major depression, bipolar disorder (sometimes called manic-depressive illness), and dysthymia, a less severe form of depression. Major depression is manifested by a combination of symptoms that interfere with the ability to work, study, sleep, eat and enjoy once pleasurable activities. Bipolar disorder, which is not nearly as prevalent as other forms of depressive disorders, is characterized by cycling mood changes. Dysthymia, a less severe type of depression, involves long-term, chronic symptoms that do not disable, but keep one from functioning well or from feeling well. Depression also includes temporary sadness and loneliness often felt from time to time. Use of the extended cycle regimen, compared to use of a conventional 28-day contraceptive regimen, can lead to a reduction in the reported occurrences of non-menstrual related depression. Thus, the disclosed extended cycle regimen can be used as a method of preventing or treating non-menstrual related depression.

The invention is also directed to a method of providing contraception and treating depression unrelated to the menstrual cycle in a female in need thereof by administering to the female the extended cycle regimen disclosed herein. The female can be, for example, of childbearing age or peri-menopausal.

The invention is further directed to a method of increasing contraceptive effectiveness in a female in need thereof by administering to the female the extended cycle regimen disclosed herein. The female can be, but is not limited to, a female of childbearing age or a peri-menopausal female. A female in need of contraceptive effectiveness can be, but is not limited to, a higher weight female. A "higher weight female" refers to a human female weighing about 70 kg or more or having a body mass index (BMI) of greater than about 25. In a recent study of body weight and oral contraceptive failure, women weighing about 70.5 kg or more were reported to have a 60% higher risk of oral contraceptive failure (Holt, V. L., et al., *Obstet. Gynecol.* 99:820-827 (2002)). In a study utilizing the extended cycle regimen, women who weighed about 70 kg or more experienced the same contraceptive effectiveness as women on the same extended cycle regimen who weighed less than about 70 kg.

Thus, the invention is directed to a method of increasing contraceptive effectiveness in a higher-weight female in need thereof, by administering to the female the extended cycle regimen disclosed herein. The invention is directed to a method of increasing the contraceptive effectiveness in a human female weighing about 70 kg or more, weighing 80 kg or more, or weighing 90 kg or more, by administering to the female the extended cycle regimen.

The disclosed extended cycle regimen can also be used as a method of increasing the contraceptive effectiveness in a human female with a body mass index of greater than about 25, greater than about 30, or greater than about 35. Thus, the invention is also directed to a method of increasing the contraceptive effectiveness in a human female with a body mass index of greater than about 25, greater than about 30, or greater than about 35, by administering to the female the extended cycle regimen.

The invention is also directed to a method of increasing fertility in a female in need thereof, by administering to the female the extended cycle regimen disclosed herein, followed by administration of an agent to induce ovulation in the female. The female can be, but is not limited to, a female of childbearing age or a peri-menopausal female.

It has been observed clinically that women who are taking oral contraceptives for anovulation often conceive when pills are missed, or shortly after discontinuing oral contraceptive treatment, most likely due to a "rebound effect" occurring in the ovary at least for a short period of time. Suppression of ovarian activity using oral contraceptive pills for 2-6 months may result in decreases in early follicular ovarian androgen production and LH and estradiol levels. Increased androgen levels have been shown to have adverse effects on folliculogenesis. These endocrine changes in the early follicular phase may be responsible for improved ovarian response to clomiphene or other treatments for anovulatory infertility. See Brannigan, E. F., and Estes, M. A., *Am. J. Obstet. Gynecol.* 188:1424-1430 (2003).

Examples of agents that induce ovulation, and that can be administered following the disclosed extended cycle regimen, include, but are not limited to, menotropins (Follicle Stimulating Hormone (FSH) and Luteinizing Hormone (LH), e.g., Pergonal®) and chlomiphene citrate (Clomid®).

In some aspects of the invention, the disclosed extended cycle regimen is particularly useful in peri-menopausal women and/or menopausal women. Peri-menopausal and menopausal women frequently experience a large variety of conditions and disorders that have been attributed to estrogen deprivation due to ovarian failure or hypoestrogenism. The duration of these disorders can be extremely variable and include hot flushes which can be devastating in some women and very mild in others. Dryness of the vagina associated with susceptibility to minor infections, and frequently associated with discomfort during intercourse, is another symptom that can be directly related to the decrease in estrogen availability.

In a long-term sense, one of the most health-threatening aspects of menopause is the loss of mineral from bone which can result in a decrease in bone mass (osteoporosis) and generates a serious risk of fractures. For example, evidence exists that there is a six-fold increase in fractures in post-menopausal women as opposed to men of the same age (Garraway et al., *Mayo Clinic Proceedings* 54:701-707 (1979)). These fractures, of course, carry a high complication rate among older people, a marked increase in disability and general morbidity, and certainly an increased risk of mortality.

Another serious health-threatening aspect of menopause is the impressive loss of protection against heart attacks, which is enjoyed by younger women up to the age of 60, when compared to men of the same age. The steep increase in mean serum cholesterol concentration, which occurs around menopause (during the fourth and fifth decades), can contribute importantly to the progressive increase in death from ischemic heart disease in older women. In the eighth and ninth decades, the incidence of deaths from ischemic heart disease, approaches that of men (Havlik, R. J. and Manning-Feinleid, P. H., NIH Publication No. 79-1610, U.S. Department of HEW (1979)).

Accordingly, the invention is directed to a method for treating conditions, such as the physical conditions described above, resulting from menopausal estrogen decline in a menopausal female in need thereof by administering the extended cycle regimen disclosed herein to the female. The invention is also directed to a method for treating conditions, such as the physical conditions described above, resulting from hypoestrogenism in a female in need thereof by administering the extended cycle regimen disclosed herein to the female. The invention is further directed to a method for treating conditions, such as the physical conditions described above, resulting from ovarian failure in a female in need thereof by administering the extended cycle regimen disclosed herein to the female.

The invention is also directed to a method of providing contraception and treating conditions, such as the physical conditions described above, resulting from hypoestrogenism in a peri-menopausal female in need thereof by administering the extended cycle regimen disclosed herein to the peri-menopausal female. The invention is further directed to a method of providing contraception and treating conditions, such as the physical conditions described above, resulting from ovarian failure in a peri-menopausal female in need thereof by administering the extended cycle regimen disclosed herein to the peri-menopausal female.

In addition to the above-mentioned major physical problems, some menopausal and peri-menopausal women experience a large variety of other symptoms ranging from depression, insomnia, and nervousness, to symptoms of arthritis and so forth.

It is generally agreed that estrogen is the most effective agent for the control or prevention of menopausal flushes and vaginal atrophy. It is effective in retarding or preventing the appearance of clinical evidence of osteoporosis. In appropriate doses, when combined with progestin, a favorable effect upon blood lipids can also be seen. Problems with estrogen therapy do exist, however, and have been widely explored and documented in the medical literature. The means by which estrogen has been administered, generally speaking, involves either the use of estrogen alone or estrogen plus a progestin.

Estrogen alone, given in small doses on a continuous basis, is effective in most patients for the control of the above symptoms and problems associated therewith. However, although the vast majority of women taking continuous low-dose estrogen will not have bleeding for many months or even years, there is a distinct risk posed by this routine of silently (i.e., exhibiting no overt symptoms) developing "hyperplasia of the endometrium." This term refers, of course, to an overstimulation of the lining of the uterus which can become pre-malignant, coupled with the possibility that the patient will eventually develop cancer of the uterine lining even under such a low-dose regimen (Gusberg et al., *Obstetrics and Gynaecology* 17:397-412 (1961)).

Estrogen alone can also be given in cycles, usually 21-25 days on treatment and 5-7 days off treatment. Again, if small doses of estrogen are required to control the symptoms and it is used to this fashion, only about 10% of women will experience withdrawal bleeding between the cycles of actual treatment. However, one must again be concerned by the risk of developing endometrial hyperplasia and by the increased relative risk of developing cancer of the uterus (Research on the Menopause: Report of a W.H.O. Scientific Group, 53-68 (1981)).

The addition of progestin with estrogen, however, as in the extended cycle regimen disclosed herein, will virtually eliminate the concern about developing endometrial hyperplasia and reduce the risk of developing endometrial carcinoma below that of the untreated general population.

Thus, the invention is directed to a method of treating a menopausal disorder or a peri-menopausal symptom in a female in need thereof by administering to the female the extended cycle regimen disclosed herein. The invention is also directed to a method of providing contraception and treating a peri-menopausal symptom in a peri-menopausal female in need thereof by administering to the female the extended cycle regimen disclosed herein.

The extended cycle regimen can be used as a method of maintaining bone density or preventing loss of bone density in a female. The extended cycle regimen can also be used in this way by administering, e.g., calcium and/or vitamin D in combination with the administration of estrogen and progestin.

The extended cycle regimen is not limited to administration to peri-menopausal or menopausal females as a method of maintaining bone density or preventing bone loss. The extended cycle regimen can also be used in a method of maintaining bone density or preventing bone loss by administration to a female of childbearing age that is not peri-menopausal or menopausal. For example, the extended cycle regimen can be used with females 12-16 years of age who have not yet achieved peak bone density, but who, due to various conditions such as anorexia, are at risk of loss of bone density or at risk of not achieving a normal physiologic bone density for age and developmental maturity.

Thus, the extended cycle regimen can also be used as a method of treating a condition in a female in need thereof resulting from menopausal or peri-menopausal estrogen decline, including osteoporosis. The extended cycle regimen can also be used as a method of providing contraception and treating a condition in a peri-menopausal female in need thereof resulting from peri-menopausal estrogen decline, including osteoporosis.

The extended cycle regimen can also be used as a method of treating a female in need of hormone replacement therapy.

Dosages and Formulations

The extended cycle regimen of the invention can include a daily dosage amount of estrogen equivalent to about 5 µg to about 50 µg of ethinyl estradiol. In some aspects of the invention, the extended cycle regimen can include a daily dosage amount of estrogen equivalent to about 5 µg to about 25 µg of ethinyl estradiol. In other aspects of the invention, the extended cycle regimen can include a daily dose of estrogen equivalent to about 25 µg to about 40 µg of ethinyl estradiol. In yet other aspects of the invention, the extended cycle regimen can include a daily dose of estrogen equivalent to about 10 µg to about 30 µg of ethinyl estradiol. In some aspects of the invention, the extended cycle regimen can include a daily dose of estrogen equivalent to about 20 µg of ethinyl estradiol.

The extended cycle regimen of the invention can include a daily dosage amount of progestin equivalent to about 0.01 mg to about 1.5 mg of levonorgestrel. In some aspects of the invention, the extended cycle regimen can include a daily dosage amount of progestin equivalent to about 0.01 mg to about 0.25 mg of levonorgestrel. In other aspects of the invention, the extended cycle regimen can include a daily dose of progestin equivalent to about 0.05 mg to about 0.20 mg of levonorgestrel. In other aspects, the extended cycle regimen can include a daily dose of progestin equivalent to about 0.15 mg of levonorgestrel. In yet other aspects of the invention, the extended cycle regimen can include a daily dose of progestin equivalent to about 0.1 mg of levonorgestrel.

In some aspects of the invention, the estrogen and progestin of the extended cycle regimen can be ethinyl estradiol and levonorgestrel, respectively, although other useful estrogens and progestins can be employed. The weight ratio of estrogen and progestin can be about 1:0.2 to about 1:300. In some aspects of the invention, the weight ratio of estrogen and progestin is about 1:1 to about 1:50. In other aspects of the invention, the weight ratio of estrogen and progestin is about 1:1 to about 1:10. For example, the daily amount of ethinyl estradiol is about 10 µg to about 30 µg and the daily amount of levonorgestrel is about 0.05 mg to about 0.2 mg.

The values given above are for ethinyl estradiol and levonorgestrel, and if a different estrogen or progestin is employed, an adjustment in the amount based on the relative potency or activity can be made. Correlations in potency among the various estrogens and among the various progestins are known. See, for example, EP 0 253 607, which is hereby incorporated in its entirety by reference. For example, in a contraceptive regimen, 30 µg of ethinyl estradiol is roughly equivalent to about 60 µg of mestranol or about 2,000 µg of 17β-estradiol. Similarly, 0.050 mg of levonorgestrel is roughly equivalent to about 0.175 mg of norethindrone acetate, about 0.050 mg of desogestrel, about 0.050 mg 3-ketodesogestrel, about 0.035 mg of gestodene, or about 0.100 mg of norgestrel. It should be understood that when norgestrel is used in place of levonorgestrel, its concentration is twice that of levonorgestrel. Norgestrel (dl-norgestrel) is a racemic mixture of optically active isomers, while levonorgestrel is one of the optically active isomers present in norgestrel.

Equivalent concentrations of estrogens and of progestins can be determined using either in vitro or in vivo assay methods. See, for example, Kuhl, H., *Drugs* 51(2):188-215 (1996); Philibert, D., et al., *Gynecol. Endocrinol.* 13:316-326 (1999); and Lundeen, S., et al., *J. Steroid Biochem. Molec. Biol.* 78:137-143 (2001), in which the relative potencies of various progestins are compared using both in vitro and in vivo test assays. See also, for example, Dickey, R. P., "Contraceptive Therapy," *OBG Management Supplement* (October 2000), pp. 2-6. Each of these documents is hereby incorporated by reference in its entirety.

For example, various combinations of progestin and estrogen that have been used in oral contraceptives are shown in Table 1.

TABLE 1

Combinations of Progestin and Estrogen

| Progestin | Norethindrone | | Estrogen | EE Equivalent | | |
|---|---|---|---|---|---|---|
| | Dose (mg) | Equivalent Dose (mg) | | Dose (mg) | Dose (mg) | P/E Ratio |
| Norethynodrel | 9.85 | 9.85 | Mestranol | 0.150 | 0.105 | 93.810 |
| | 5.00 | 5.00 | | 0.075 | 0.053 | 95.238 |
| | 2.50 | 2.50 | | 0.036 | 0.025 | 99.206 |
| | 2.50 | 2.50 | | 0.100 | 0.070 | 35.714 |
| Norethindrone | 10.00 | 10.00 | Mestranol | 0.060 | 0.042 | 238.095 |
| | 2.00 | 2.00 | | 0.100 | 0.070 | 28.571 |
| | 1.00 | 1.00 | | 0.050 | 0.035 | 28.571 |
| | 1.00 | 1.00 | | 0.080 | 0.056 | 17.857 |
| Norethindrone | 1.00 | 1.00 | Ethinyl | 0.050 | 0.050 | 20.000 |
| | 1.00 | 1.00 | estradiol | 0.035 | 0.035 | 28.571 |
| | 0.50 | 0.50 | (EE) | 0.035 | 0.035 | 14.286 |
| | 0.40 | 0.40 | | 0.035 | 0.035 | 11.429 |
| Norethindrone acetate | 2.50 | 2.50 | EE | 0.050 | 0.050 | 50.000 |
| | 1.00 | 1.00 | | 0.050 | 0.050 | 20.000 |
| | 0.60 | 0.60 | | 0.030 | 0.030 | 20.000 |
| | 1.50 | 1.50 | | 0.030 | 0.030 | 50.000 |
| | 1.00 | 1.00 | | 0.020 | 0.020 | 50.000 |
| Ethynodiol diacetate | 1.00 | 1.00 | Mestranol | 0.100 | 0.070 | 14.286 |
| Ethynodiol diacetate | 1.00 | 1.00 | EE | 0.050 | 0.050 | 20.000 |
| | 1.00 | 1.00 | | 0.035 | 0.035 | 28.571 |
| di-Norgestrel | 0.50 | 0.75 | EE | 0.050 | 0.050 | 10.000 |
| | 0.30 | 0.45 | | 0.030 | 0.030 | 10.000 |
| Levonorgestrel | 0.10 | 0.35 | EE | 0.020 | 0.020 | 5.000 |
| | 0.15 | 0.52 | | 0.030 | 0.030 | 5.000 |

Equivalencies
50 mg Mestranol = approx. 35 mg Ethinyl estradiol (EE)
0.1 mg dl-Norgestrel = approx. 0.15 mg Norethindrone Each block in Table 1 describes a specific combination of progestin and estrogen, e.g., norethynodrel and mestranol, and within each block older combinations are listed first, with successively newer combinations following.

Suitable progestins for use in the present invention include, but are not limited to, natural and synthetic compounds having progestational activity, such as, for example, progesterone, chlormadinone acetate, norethindrone, cyproterone acetate, norethindrone acetate, desogestrel, levonorgestrel, drospirenone, trimegestone, norgestrel, norgestimate, norelgestromin, etonogestrel, gestodene, and other natural and/or synthetic gestagens. Prodrugs of suitable progestins can also be used in the extended cycle regimen of the present invention.

The expression "prodrug" denotes a derivative of a known direct acting drug, which derivative has enhanced delivery characteristics and therapeutic value as compared to the drug and is transformed into the active drug by an enzymatic or chemical process. Ethynodiol diacetate, which is converted in vivo to norethindrone, is an example of a progestin prodrug that can be used in the present invention. Additional examples of progestin prodrugs include, but are not limited to, norgestimate (which is converted in vivo to 17-deacetyl norgestimate, also known as norelgestromin), desogestrel (which is converted in vivo to 3-keto desogestrel, also known as etonogestrel), and norethindrone acetate (which is converted in vivo to norethindrone).

Suitable estrogens in the present invention include, but are not limited to, natural and synthetic compounds having estrogenic activity, such as, for example, estradiol (17β-estradiol), 17α-estradiol, estriol, estrone, and their esters, such as the acetate, sulfate, valerate or benzoate esters of these compounds, including, for example, estradiol 17β-cypionate, estradiol 17-propionate, estradiol 3-benzoate, and piperazine . estrone sulfate; ethinyl estradiol; conjugated estrogens (natural and synthetic); mestranol; agonistic anti-estrogens; and selective estrogen receptor modulators. Prodrugs of suitable estrogens can also be used in the extended cycle regimen of the present invention. Examples of estrogen prodrugs that can be used in the present invention include, but are not limited to, estradiol acetate (which is converted in vivo to 17β-estradiol) and mestranol (which is converted in vivo to ethinyl estradiol).

The estrogen and progestin are administered in the conventional manner by any route where they are active. For example, administration can be by, but is not limited to, parenteral, subcutaneous, intravenous, intramuscular, intraperitoneal, transdermal, buccal, or ocular routes, or intravaginally, by inhalation, by depot injections, or by hormone implants. Thus, modes of administration for the estrogen and progestin (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams.

Most estrogens and progestins are orally active and this route of administration can be used in the invention. Accordingly, administration forms can include, but are not limited to, tablets, dragees, capsules and pills, which contain the estrogen and the progestin and one or more suitable pharmaceutically acceptable carriers.

For oral administration, the estrogen and progestin can be formulated readily by combining these compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the estrogen and progestin compositions can take the form of, e.g., tablets or lozenges formulated in a conventional manner.

For administration by inhalation, the estrogen and progestin for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The estrogen and progestin can be formulated for parenteral administration by injection, e.g., by bolus injection or continuous infusion. The compounds can be administered by continuous infusion subcutaneously over a period of about 15 minutes to about 24 hours. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example subcutaneously or intramuscularly) or by intramuscular injection. Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The pharmaceutical compositions of the estrogen and progestin also can comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

In transdermal administration, the estrogen and progestin components, for example, can be applied to a plaster, or can be applied by transdermal, therapeutic systems that are consequently supplied to the organism.

The combination of estrogen and progestin can also be administered in combination with other active ingredients. For example, estrogen and progestin can be administered with vitamin D and/or calcium in the extended cycle regimen as a method of maintaining or preventing loss of bone density. The form of vitamin D and of calcium used in the present invention would be well known to those of skill in the art, as would the amount. For example, calcium can be administered in the form of calcium carbonate, at a daily dosage level of 500 mg.

Thus, pharmaceutical formulations containing the estrogen and progestin and a suitable carrier can be solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of estrogen and progestin as taught in this invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, "Modern Pharmaceutics", Banker & Rhodes, Marcel Dekker, Inc. 1979; and "Goodman & Gilman's The Pharmaceutical Basis of Therapeutics," $6^{th}$ Edition, MacMillan Publishing Co., New York 1980 can be consulted.

The contraceptive preparations can be produced in the form of a kit or package, with the daily dosages arranged for proper sequential administration. For example, in some aspects of the invention, e.g., in the oral form of the formulation, the present invention provides a pharmaceutical package which contains combination-type contraceptives in multiple dosage units in a synchronized, fixed sequence, wherein the sequence or arrangement of the dosage units corresponds to the stages of daily administration.

Thus, for example, the pharmaceutical formulations useful in the invention can be provided in kit form containing at least about 50 tablets intended for ingestion on successive days, followed by about 2 to about 10 tablets, intended for ingestion on successive days. Administration is daily for at least 50 consecutive days using tablets containing the both the estrogen and the progestin, and is followed by administration that is daily for about 2 to about 10 consecutive days using hormone-free placebo tablets. For example, administration can be for 60-110 consecutive days, using tablets containing both estrogen and the progestin, followed by administration for at least 2-10 days, using hormone-free placebo tablets.

In another example, the pharmaceutical formulations can be provided in kit form containing, e.g., for a 91-day regimen, 84 tablets, each tablet containing estrogen and progestin, intended for ingestion on successive days, followed by 7 hormone-free placebo tablets, intended for ingestion on successive days.

All of the various aspects, embodiments and options described herein can be combined in any and all variations. The extended cycle regimen disclosed herein can be administered to females of child-bearing age, peri-menopausal females, or menopausal females as needed for treatment of any of the conditions and disorders described above.

The following examples are illustrative, but not limiting, of the method and compositions of the present invention. Other suitable modifications and adaptations of the variety of conditions and parameters normally encountered and obvious to those skilled in the art are within the spirit and scope of the invention. Thus, the breadth and scope of the present invention should not be limited by any of the above-described exemplary embodiments, but should be defined only in accordance with the following claims and their equivalents.

EXAMPLE 1

This example provides detailed results of a randomized clinical study evaluating a 91-day extended cycle oral contraceptive (OC) containing 84 days of 30 µg ethinyl estradiol (EE) and 150 µg levonorgestrel (LNG) followed by 7 days of placebo.

Materials and Methods
Study Design and Population

This was a parallel, randomized, multicenter, open-label study of a 91-day extended cycle OC (30 µg EE/150 µg LNG) and Nordette® (30 µg EE/150 µg LNG). Eligible women were randomized in a 2:1 fashion to the 91-day extended cycle OC or Nordette®. Study therapy was administered for one year (four consecutive cycles of the 91-day extended cycle regimen or 13 consecutive cycles of 28-day (conventional) cycle regimen). In the same study design, patients could also be randomized to a second 91-day extended cycle OC having a lower concentration of ethinyl estradiol (20 µg EE/100 µg LNG) or Levlite®. The intent of the study was to compare the effects of like dosage levels of the 91-day extended cycle regimen to conventional 28-day cycles within the context of separate pair-wise comparisons. This report presents results for the higher dosage levels of the extended and conventional cycle regimens.

The study was performed in accordance with the Declaration of Helsinki (Republic of South Africa, 1996), applicable guidelines for Good Clinical Practice and with ethics committee approval at each participating clinical site.

Sexually active, adult women (age 18 through 40), of childbearing potential, in a heterosexual relationship, who were at risk for pregnancy, fluent in English, and able to give informed consent were eligible for the study. Active smokers >35 years old were excluded, as were women with any contraindication to the use of OCs, those who had received injectable hormone therapy (e.g., Depo-Provera®) within the 10 months prior to study enrollment, had a progestin-releasing intrauterine device (IUD) in place within three months prior to enrollment, or a contraceptive implant removed within one month prior to enrollment. Routine use of other forms of contraception other than OCs (with the exception of condoms) was also an exclusion to study entry. Those with a recent surgical or medical abortion, miscarriage, or vaginal or cesarean delivery must have had at least two normal menstrual cycles prior to enrollment. Other exclusions included history of abnormal bleeding (breakthrough or withdrawal bleeding that lasts 10 or more consecutive days, or spotting that lasts more than 10 consecutive days) while on conventional OCs, participation in any clinical investigation within 30 days prior to enrollment, and donation or sustained a loss of more than 500 mL of blood within 30 days prior to enrollment. Prohibited medications included use of any medication that might interfere with the efficacy of OCs (e.g., rifampin, barbiturates, antibiotics). At the time of entry into the study, patients were designated as continuous users (those who were on OCs during the cycle prior to entering the study), fresh starts (those with no prior history of OC use), or prior users (those who had a history of OC use in the past without having any OC use in the 6 months prior to enrollment).

Patients could have discontinued from the study for any of the following reasons: any condition that contraindicated the use of OCs, patient decision, pregnancy, any adverse event that made continuation in the study impossible or inadvisable, lost to follow-up, discovered after enrollment not to have met study criteria, refusal to cooperate with required study procedures, or significant lapse of study medication intake (i.e., <80% overall pill taking).

Dosing Regimen and Procedures

Patients randomized to the extended cycle regimens were given blister packs with a 91-day supply of study medication (84 active pills and 7 placebo) at each clinic visit. Four pill packs were dispensed during the one-year study. Patients randomized to the conventional 28-day regimen were supplied with three or four commercial pill packs at each clinic visit, depending on the study month when the next scheduled clinic visit was to take place. All patients received copies of patient instructions for use with each supply of study medication. They were also instructed to return all used pill packs and pill counts were conducted at each clinic visit.

Screening prior to initiation of study therapy and after obtaining informed consent included a medical and contraceptive history, physical examination (including pelvic exam and Pap smear), measurement of vital signs (including weight), clinical laboratory tests (CBC, serum chemistry, lipid profile, and urinalysis), and a urine pregnancy test. Urine pregnancy tests were also obtained at all clinic visits after baseline and at the time of study completion or patient discontinuation.

All patients enrolled in the study completed a daily electronic diary. Questions regarding pill-taking, and occurrence and severity of bleeding/spotting were recorded daily, while responses regarding concomitant contraceptive use and menstrual symptomatology were recorded weekly. All diary entries were time and date stamped to prevent retrospective completion. The diaries were programmed with a reminder alarm in the event more than 24 hours lapsed between diary entries. Patients were provided with paper diaries listing the same questions in the event of electronic diary failure or loss. Concomitant medications and adverse events were recorded separately. At each clinic visit all data from the electronic diaries were downloaded into the investigational site's study database and into a centralized database maintained by the diary vendor.

All patients were to initiate OC therapy on the first Sunday following the beginning of their menstrual period or withdrawal bleed from prior oral contraceptive cycle ("Sunday starters") and were to remain as Sunday starters throughout the study. They were counseled to take their pill at approximately the same time each day and to record pill intake in the electronic diaries on a daily basis. There were no dosage adjustments, other than in the event that pills were missed.

Patients were seen approximately every three months during the course of the study and at the end of the study. Any patient who withdrew or who was withdrawn from the study had an end-of-study evaluation completed in the same manner as those who completed the full term of study participation. All patients were followed for two months for the occurrence of pregnancy following completion of the study or early withdrawal. Patients who became pregnant were followed for eight weeks following delivery or termination of the pregnancy. Infants were followed for eight weeks following delivery. Compliance with study medication was assessed by daily self-reporting by the patient in electronic or paper diaries. "Compliant use" was defined by eliminating all cycles in which a patient skipped two or more consecutive pills, had a pattern of substantial non-compliance (<80% overall pill-taking), used alternative forms of contraception (including emergency contraceptives), or used prohibited concomitant medications that interact with OC therapy. "Compliant use" patients were also restricted to those patients between the ages of 18 and 35 years, according to the US Food and Drug Administration definition of "optimal" age range for ovulation (see "FDA Guidance for Industry. Combined Oral Contraceptive Labeling for Healthcare Providers and Patients," U.S. Department of Health and Human Services, Food and Drug Administration, Center for Drug Evaluation and Research (CDER), June 2000 (http://www.fda.gov/cder/guidance/2448dft.pdf).

Efficacy Assessments

Efficacy was evaluated as the method failure rate, calculated by life table analysis and the Pearl Index (the number of pregnancies per 100 women per year of use) among women age 18-35 who used the product as directed ("compliant use").

Pregnancy was defined by a positive urine pregnancy test and confirmed by serum human chorionic gonadotrophin (HCG). Conception date was calculated considering all available data such as sonogram data, quantitative HCG, qualitative HCG, pelvic examination, and delivery date. If the conception date was unknown, it was imputed as the midpoint between the patient's last negative pregnancy test date and the date of the positive pregnancy test. It was assumed that the patient was "on study" at the time of conception if the pregnancy occurred between the first and last days of study drug treatment or if the conception date was completely unknown. If conception clearly occurred before the first date of taking study medication, or more than 14 days after the last dose of study drug, it was not counted as a "during study" pregnancy.

Cycle Control Assessment

Cycle control was evaluated by observing the extent of withdrawal bleeding/spotting and breakthrough bleeding/spotting as reported in the electronic diaries. Patients were instructed that bleeding was defined as vaginal blood loss requiring the use of sanitary protection (pads or tampons). Spotting was defined as vaginal blood loss not requiring sanitary protection. All patients responded to questions regarding the presence and intensity of bleeding and/or spotting via a series of preprogrammed questions administered on a daily basis through the electronic diaries.

Bleeding and spotting during each cycle (91 days for the extended cycle regimen and 28 days for conventional regimen), and across the full year of treatment (364 days) were evaluated by assessment of total number of bleeding and/or spotting days, number of "scheduled" bleeding and/or spotting days (i.e., occurring during the 7-day placebo pill interval), and the number of "unscheduled" bleeding and/or spotting days (i.e., occurring during the 84 day active pill interval for the extended cycle regimen or during the 21-day active pill interval for the conventional regimen). Amenorrhea was defined as a lack of withdrawal bleeding during placebo pill intervals.

Evaluation of scheduled bleeding days (i.e., that occurring during the placebo pill interval over the course of one year's treatment) was based on a total of 28 possible days for the extended cycle regimen versus 91 possible days for the conventional regimen. Evaluation of unscheduled bleeding days (i.e., that occurring during the active pill interval) was based on a total of 336 possible days for the extended cycle regimen versus 273 possible days for the conventional regimen.

Safety Assessment

Safety was evaluated by assessment of self-reported adverse events and adverse events elicited at clinic visits, clinical laboratory tests, vital signs (including weight), and physical examination. All patients who took the study drug were included in the safety assessment. A cohort of patients from the extended cycle regimen groups underwent endometrial biopsy prior to initiation of study medication, and again at the completion of the study to assess the effect of an extended oral contraceptive cycle on the endometrium. A case report form (CRF) was used to formally record all information regarding reported adverse events. Adverse events were reported spontaneously by the patients, primarily during the regularly scheduled study visit but also by way of the patient's daily diary. For each adverse event, clinical site personnel (a physician or nurse) obtained and recorded additional information pertaining to the seriousness of the adverse event, its severity (mild, moderate, severe, life-threatening), its onset and resolution dates, whether it was still ongoing, the action taken as a result of the event (e.g., no action taken, medical/surgical treatment, interruption of study drug, study discontinuation), and the outcome of the event on the patient's participation in the study (e.g., no effect on participation, study discontinuation, resolution with or without sequalae, death). Verbatim reported adverse events were classified by body system and preferred term using the MedDRA 4.0 coding nomenclature, a well recognized and standardized system for reporting the incidence and prevalence of adverse events in clinical trials conducted across all therapeutic areas.

Statistical Methods

For this multicenter study, data were pooled across centers. No formal statistical tests were conducted, but descriptive statistics were computed. Life table estimates of the cumulative rate of pregnancy at 52 weeks used 4-week (28-day) intervals for the conventional cycle regimen and 91-day intervals for the extended cycle regimen. Two-sided 95% percent confidence intervals were computed about each cycle's point estimate of the cumulative pregnancy rate. Since the life-table approach is based on a continuous time interval, it includes a patient's entire term of participation in the study, not just completed cycles. The Pearl Index was calculated by dividing the number of on-treatment pregnancies by the total number of complete cycles of exposure (91 days for the extended cycle regimen, and 28 days for the conventional regimen) and expressing the result as an annualized estimate per 100 subjects. The cycles of exposure also included any cycle when a pregnancy occurred.

Results

Study Population and Disposition

A total of 682 patients were randomized to either to the 91-day extended cycle OC or Nordette® conventional regimen across 47 study sites located throughout the United States. The demographic characteristics of the patients in these treatment groups are presented in Table 2. The two study groups were comparable in terms of racial distribution, mean age, weight, body mass index, smoking status and history of OC use. Over 60% of the patients studied were continuous OC users and an additional 30% had a history of prior OC use but were not on OCs at the time of enrollment ("prior users"). Less than 10% of patients had no history of OC use ("fresh starts").

Overall, 59.4% (271/456) of extended cycle regimen patients and 71.2% of conventional regimen patients (161/226) completed one year of therapy on-study. The most common reasons for premature discontinuation were adverse events, individual patient decision, and "lost to follow-up." The most common adverse events cited as a reason for study discontinuation were bleeding, increased weight, mood swings, and acne. Discontinuation for "unacceptable bleeding" whether cited as an adverse event or as an individual patient decision, accounted for 7.7% of extended cycle regimen patients and 1.8% of conventional regimen patients. For extended cycle regimen patients, the rate of discontinuation due to unacceptable bleeding decreased considerably after week 26 (i.e., following two extended cycles).

TABLE 2

Demographic characteristics of study patients (N = 682)

| Characteristic | Extended cycle regimen (n = 456) | Conventional regimen (n = 226) |
|---|---|---|
| Race; n (%) | | |
| Caucasian | 351 (77.0) | 169 (74.8) |
| African American | 50 (11.0) | 29 (12.8) |
| Asian | 10 (2.2) | 2 (0.9) |
| Hispanic | 32 (7.0) | 18 (8.0) |
| Other | 13 (2.9) | 8 (3.5) |
| Age (year) | | |
| Mean (SD) | 27.8 (5.89) | 27.83 (5.9) |
| (range) | (18-40) | (19-40) |
| Weight (lb) | | |
| Mean (SD) | 156.39 (38.04) | 156.58 (38.7) |
| (range) | (84-304) | (87-296) |
| Body mass index (kg/m2) | | |
| Mean (SD) | 26.16 (5.9) | 26.31 (6.3) |
| (range) | (14.47-45.29) | (16.0-47.5) |
| Current smoker? | | |
| No (%) | 373 (81.8) | 191 (84.5) |
| Yes (%) | 83 (18.2) | 35 (15.5) |
| OC use history; n (%) | | |
| Unknown | 1 (0.2) | 0 (0.0) |
| Continuous | 288 (63.2) | 142 (62.8) |
| Fresh Start | 35 (7.7) | 14 (6.2) |
| Prior User | 132 (29.0) | 70 (31.0) |

Compliance

There were two measurements of compliance, which were evaluated by assessing patient diary data as to whether or not they took their OC pill every day. Pill compliance within each extended or conventional cycle was determined by observing if the patient missed two consecutive days of pill taking and, if so, the patient was considered to be non-compliant for that cycle. Overall study compliance was determined by counting the percentage of total days in the one-year study when the patient took the designated pill for a given day. Overall compliance of less than 80% would exclude a patient altogether from the Pearl Index calculation. Otherwise, non-compliance within a particular cycle would exclude that cycle only from the Pearl Index. For the life-table calculation, only the overall compliance criterion was used to exclude "non-compliant" patients from the cumulative pregnancy rate calculation, since exclusion of individual cycles from the patient's total would lead to a non-continuous, intermittently truncated time frame.

The overall treatment compliance rate in each of the study groups was very high with 95.4% of extended cycle regimen patients and 93.4% of conventional regimen patients assessed as compliant. A total of 22 (4.8%) extended cycle regimen patients and 9 (4.0%) conventional regimen patients were discontinued from the study due to non-compliance. The number of clinically significant protocol deviations was minimal and no protocol deviations were used to exclude any patients from the analysis of efficacy or safety. Most protocol deviations were related to inclusion/exclusion criteria at study enrollment and were not observed during the active study interval.

Efficacy

Among those patients between the ages of 18 and 35 years, a total of 397 (mean age 26.4 years) received the extended cycle regimen and 195 (mean age 26.2 years) received the conventional regimen. During the course of the study, seven (7) patients became pregnant, 4 of 456 (0.9%) treated with the extended cycle regimen and 3 of 226 (1.3%) treated with the conventional regimen. Diary data indicated use of other methods of birth control and/or noncompliance with study medication around the estimated date of conception for three of four extended cycle regimen patients and one of three conventional regimen patients. Thus, one extended cycle and two conventional cycle regimen-reported pregnancies were considered method failures. Pearl Index calculations based on method failure were 0.60 for the 91-day extended cycle OC and 1.78 for Nordette®. Life table point estimates among compliant use patients were 0.55 per 100 women for the 91-day extended cycle OC and 1.45 per 100 women for Nordette®. Body weight >90 kg was not a contributing factor in this calculation as no patient weighing more than 90 kg became pregnant.

Cycle Control

Total Number of Days of Bleeding

The median observed total number of days (out of a possible 364 days) of reported bleeding and/or spotting for all patients enrolled in the study (ITT population) was 35 for the extended cycle regimen versus 53 for the conventional regimen. Among patients treated with the extended cycle regimen, more than half of the total number of days were attributed to spotting. A greater percentage of bleeding only days were reported with the conventional regimen (median 12.2%) versus the extended cycle regimen (median 5.7%).

Scheduled Withdrawal Bleeding

Due to the differences in the number of cycles of treatment between the 91-day extended cycle treatment and the 28-day conventional regimen (4 vs. 13), and the number of annual hormone free days (28 vs. 91), patients on the extended cycle regimen had fewer total days of scheduled (withdrawal) bleeding/spotting than did patients treated with the conventional regimen. On a per cycle basis, the median number of days of withdrawal bleeding was similar in both treatment groups. When expressed as a percentage of the total possible days of withdrawal bleeding (28 days for the extended cycle regimen vs. 91 days for the conventional regimen), the median percent of scheduled withdrawal bleeding and/or spotting and bleeding-only days was similar in the two treatment groups.

Unscheduled (Breakthrough) Bleeding

Figure 2:
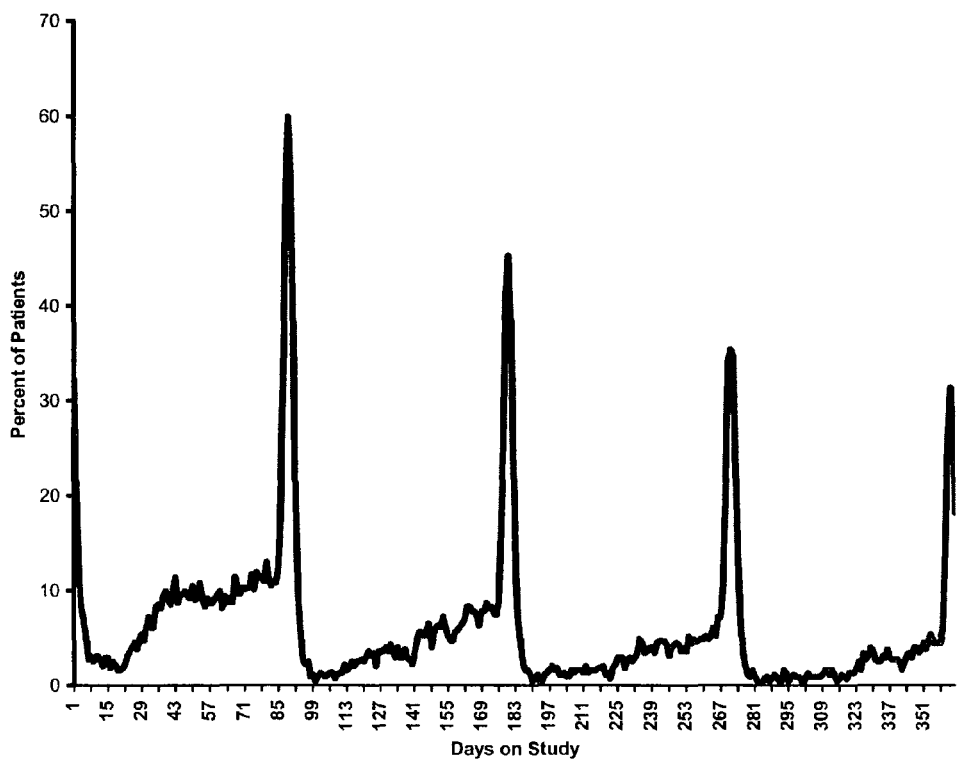
FIG. 2 shows the percent of patients on the 91-day extended regimen reporting bleeding by study day for the clinical study described in Example 1.

Like all OC products, patients who received the extended cycle regimen reported varying degrees of breakthrough bleeding (BTB). The active treatment duration of each extended cycle was four times the length of the active treatment duration for each conventional cycle (84 days vs. 21 days). Within the extended cycle regimen treatment group, there were fewer days of BTB with each successive cycle from a median of 12 days during cycle 1 to a median of 4 days during cycle 4. (FIG. 1). The onset of BTB also occurred later within each successive extended cycle and was of shorter duration with each successive extended cycle. The median number of days of unscheduled bleeding-only days in each cycle, as well as the percentage of patients reporting unscheduled bleeding in each cycle, decreased throughout the course of the study as depicted in FIG. 2.

Extended cycle regimen patients initially reported slightly more breakthrough bleeding and/or spotting and bleeding only than did patients treated with the conventional regimen. By the last extended cycle (cycle 4), breakthrough bleeding was comparable in the two treatment groups. Of the total number of possible days of unscheduled bleeding or spotting days that could be reported (active therapy days: 336 for the extended cycle regimen vs. 273 days for the conventional regimen), a median of 3.6% days on the extended cycle regimen and 2.9% days on the conventional regimen were associated with diary entries of unscheduled bleeding.

The majority of patients in both treatment groups reported 5 or less days of unscheduled bleeding per cycle. By the end of the study (cycle 4), 41.5% of extended cycle regimen patients reported no unscheduled bleeding and more than 80% had 5 days or less. The percentage of patients reporting higher numbers of unscheduled bleeding days ($\geq 6$) also decreased with each successive cycle of therapy.

Safety

The incidence rates of adverse events (AEs) were comparable across the treatment groups. AEs reported with the highest incidence rates were those associated with sinus and respiratory tract infections (usually reported by the patient as cold or flu symptoms), headache, and "unexpected" or "breakthrough" bleeding. The incidence of headache was lower for extended cycle regimen patients than for conventional regimen patients (21% vs. 28%). However, higher incidence rates of bleeding-reported events were observed for extended cycle regimen patients than for conventional regimen patients (12% vs. 3%). It should be noted that there was no correlation between "bleeding" reported as an adverse event, "bleeding" reported in the electronic diary, and "bleeding" given as a patient-specified reason for study discontinuation. Shifts in mean laboratory values from baseline to end of study were similar to those reported with other OC therapies ("FDA Guidance for Industry. Combined Oral Contraceptive Labeling for Healthcare Providers and Patients," U.S. Department of Health and Human Services, Food and Drug Administration, Center for Drug Evaluation and Research (CDER), June 2000 (http://www.fda.gov/cder/guidance/2448dft.pdf)). In addition, the extended cycle group reported a lower incidence of pharyngitis (22% vs. 30%) and upper respiratory infection (URI; 6% vs. 10%) compared to the conventional regimen. A slightly smaller proportion of patients on the extended cycle regimen reported urinary tract infection (UTI) compared to the conventional cycle (4% vs. 6%). Further, 2% of extended cycle regimen patients reported one or more episodes of depression compared to 6% of patients on the conventional regimen.

Changes in triglycerides and LDL cholesterol were comparable between the two treatment groups. There were no clinically meaningful changes in other laboratory values, body weight, vital signs (systolic and diastolic blood pressure, heart rate, or temperature) or in physical exam results from baseline to end of study. There were no reports of endometrial hyperplasia or carcinoma.

Discussion/Conclusions

This was the first large-scale controlled study of an extended cycle OC regimen in women up to age 40. The extended cycle regimen consists of a known combination of ethinyl estradiol and levonorgestrel administered at a dose level with a history of proven efficacy and safety. When taken daily, the extended regimen OC was effective in preventing pregnancy. The adverse event profiles of the extended cycle regimen and the conventional regimen were comparable and similar to those of other oral contraceptives ("FDA Guidance for Industry. Combined Oral Contraceptive Labeling for Healthcare Providers and Patients," U.S. Department of Health and Human Services, Food and Drug Administration, Center for Drug Evaluation and Research (CDER), June 2000 (http://www.fda.gov/cder/guidance/2448dft.pdf)). The electronic diaries utilized in this study provided a daily "snapshot" of pill compliance and cycle control that is more detailed than any previously published reports.

Noncompliance with pill-taking is particularly troublesome during the transition from one package to the next, an occurrence that takes place 13 times per year with conventional therapy (Adams, H. P. J., "Oral contraception noncompliance: The extent of the problem," *Adv. Contracept.* 8(suppl 1):13-20 (1992)). With the use of the extended cycle regimen, the number of transitions between packs is decreased to 4 per year, which can contribute to improved compliance. In this study, compliance with both treatment regimens was very high, possibly due, in part, to daily reminders regarding pill-taking conveyed via use of the electronic diary.

All OCs are associated with unscheduled breakthrough bleeding during the active pill phase. (See "FDA Guidance for Industry. Combined Oral Contraceptive Labeling for Healthcare Providers and Patients," U.S. Department of Health and Human Services, Food and Drug Administration, Center for Drug Evaluation and Research (CDER), June 2000 (http://www.fda.gov/cder/guidance/2448dft.pdf)). It is also well recognized that breakthrough bleeding diminishes with continued use of OCs. This pattern of reduced incidence of unscheduled bleeding with consecutive cycles of OCs was replicated in this study. Both the median number of days of unscheduled bleeding and/or spotting days as well as the percentage of patients reporting unscheduled bleeding and/or spotting decreased throughout the course of the study in both treatment groups. While the incidence of unscheduled bleeding was higher among patients treated with the extended cycle regimen early in the study, it decreased with each successive cycle of therapy. By the end of the study, the median incidence of unscheduled bleeding reported in the extended cycle regimen group on a patient-monthly basis was comparable to that reported in the conventional regimen group.

Clinical trials and surveys cite bleeding irregularities as the one of the most common reasons for OC discontinuation (Rosenberg, M. J., and Waugh, M. S., "Oral contraceptive discontinuation: a prospective evaluation of frequency and reasons," *Am. J. Obstet. Gynecol.* 179:577-82 (1998); WHO Task Force on Oral Contraceptives, "A randomized double-blind study of six combined oral contraceptives," *Contraception* 25:231-41 (1982)). Of note, unscheduled bleeding among patients receiving the extended cycle regimen who completed the study was the same as that observed in the ITT population. In this study, 7.7% of extended cycle regimen patients cited unacceptable bleeding as a reason for discontinuation. It is also notable that the incidence of unscheduled bleeding reported by patients who discontinued for that reason was similar to that reported in women who ultimately completed the study. Perception of severity of bleeding and acceptance of unscheduled bleeding appeared to be a personal preference. Indeed, the majority of patients rated their overall satisfaction with the extended cycle OC regimen as good to excellent and stated they would choose to have fewer menstrual periods following the completion of the study.

This study demonstrated that extended cycle OCs are effective, safe and well tolerated. The extended cycle regimen represents a change in the paradigm of OC therapy allowing women the option of decreasing the number of withdrawal bleeding intervals from 13 to 4 per year.

Having now fully described this invention, it will be understood to those of ordinary skill in the art that the same can be performed within a wide and equivalent range of conditions, formulations, and other parameters without affecting the scope of the invention or any embodiment thereof.

All documents, e.g., scientific publications, patents, patent applications and patent publications recited herein are hereby incorporated by reference in their entirety to the same extent as if each individual document was specifically and individually indicated to be incorporated by reference in its entirety. Where the document cited only provides the first page of the document, the entire document is intended, including the remaining pages of the document.

What is claimed is:

1. A method of increasing fertility in a perimenopausal female, said method consisting essentially of administering to the female a monophasic combination of estrogen and progestin for a period of 80-90 consecutive days, in which the daily amount of estrogen is equivalent to about 10 µm to about 30 µg of ethinyl estradiol and in which the daily amount of progestin is equivalent to about 0.05 mg to about 0.20 mg of levonorgestrel, followed by a hormone-free period of 5-8 consecutive days, wherein neither estrogen nor progestin is administered to the female, and wherein hormone-free placebo is administered during said hormone-free period of 5-8 consecutive days, followed by administration of an agent to induce ovulation in the perimenopausal female.

2. The method of claim 1, wherein the combination of estrogen and progestin is administered for at least 84 consecutive days.

3. The method of claim 1, wherein said hormone-free placebo is administered for 7 consecutive days.

4. The method of claim 1, wherein the agent to induce ovulation in the female is selected from the group consisting of menotropins and clomiphene citrate.

5. The method of claim 4, wherein the daily amount of estrogen is equivalent to about 30 µg of ethinyl estradiol, and the daily amount of progestin is equivalent to about 0.15 mg of levonorgestrel.

6. The method of claim 4, wherein said ovulation agent is a menotropin.

7. The method of claim 4, wherein said ovulation agent is clomiphene citrate.

* * * * *